(12) United States Patent
Yaegashi

(10) Patent No.: US 8,226,373 B2
(45) Date of Patent: Jul. 24, 2012

(54) SENSORLESS MAGNETIC BEARING TYPE BLOOD PUMP APPARATUS

(75) Inventor: Mitsutoshi Yaegashi, Tokyo (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1241 days.

(21) Appl. No.: 11/946,588

(22) Filed: Nov. 28, 2007

(65) Prior Publication Data

US 2008/0124231 A1    May 29, 2008

(30) Foreign Application Priority Data

Nov. 28, 2006  (JP) .................................. 2006-320123

(51) Int. Cl.
*F04B 49/06*  (2006.01)
(52) U.S. Cl. ..................... 417/44.11; 415/900
(58) Field of Classification Search ............ 417/423.12, 417/423.14, 423.7, 44.11, 53, 349, 354; 623/3.14; 604/151, 264; 415/900
See application file for complete search history.

(56) References Cited

U.S. PATENT DOCUMENTS

| | | | |
|---|---|---|---|
| 5,947,703 A | 9/1999 | Nojiri et al. | |
| 7,033,147 B2 * | 4/2006 | Yanai et al. | 417/410.1 |
| 7,128,538 B2 * | 10/2006 | Tsubouchi et al. | 417/12 |
| 7,138,776 B1 * | 11/2006 | Gauthier et al. | 318/400.34 |
| 7,462,019 B1 * | 12/2008 | Allarie et al. | 417/423.12 |
| 7,748,964 B2 * | 7/2010 | Yaegashi et al. | 417/420 |
| 2004/0143151 A1 | 7/2004 | Mori et al. | |
| 2005/0008496 A1 * | 1/2005 | Tsubouchi et al. | 417/44.2 |

FOREIGN PATENT DOCUMENTS

| | | |
|---|---|---|
| JP | 9-206372 A | 8/1997 |
| JP | 2004-209240 A | 7/2004 |
| WO | WO 9953974 A2 * | 10/1999 |

OTHER PUBLICATIONS

Kenichi Matsuda et al., "Self-Sensing Magnetic Levitation Control by Using the PWM Driving Method," Proceedings of the 5th Symposium of Dynamics Related to Electromagnetic Force, 1993, pp. 547-552 (with English Abstract).
Kenichi Matsuda et al., "Self-Sensing Magnetic Levitation Control by Using the PWM Driving Method," Proceedings of the 5th Symposium of Dynamics Related to Electromagnetic Force, 1993, pp. 547-552, with English language translation.

* cited by examiner

*Primary Examiner* — Devon C Kramer
*Assistant Examiner* — Amene Bayou
(74) *Attorney, Agent, or Firm* — Buchanan Ingersoll & Rooney PC

(57) ABSTRACT

A sensorless magnetic bearing type blood pump apparatus includes a blood pump and a control mechanism. The blood pump has electromagnets for rotating a rotating body in a non-contact condition, and a hydrodynamic bearing section for rotating the rotating body in a non-contact condition when operation of the electromagnets is stopped. The apparatus is devoid of any sensors for determining the position of the rotating body. The control mechanism includes a pulse width modulation type electromagnet driving unit, a carrier component measuring unit for measuring carrier components of voltage and current in the driving unit, a modulation factor calculating unit which calculates a modulation factor using the carrier wave data, and a bearing mode changing-over mechanism for effecting change-over from the magnetic bearing mode to the hydrodynamic bearing mode when the calculated modulation factor is outside a predetermined range and for returning to the magnetic bearing mode after the change-over.

13 Claims, 23 Drawing Sheets

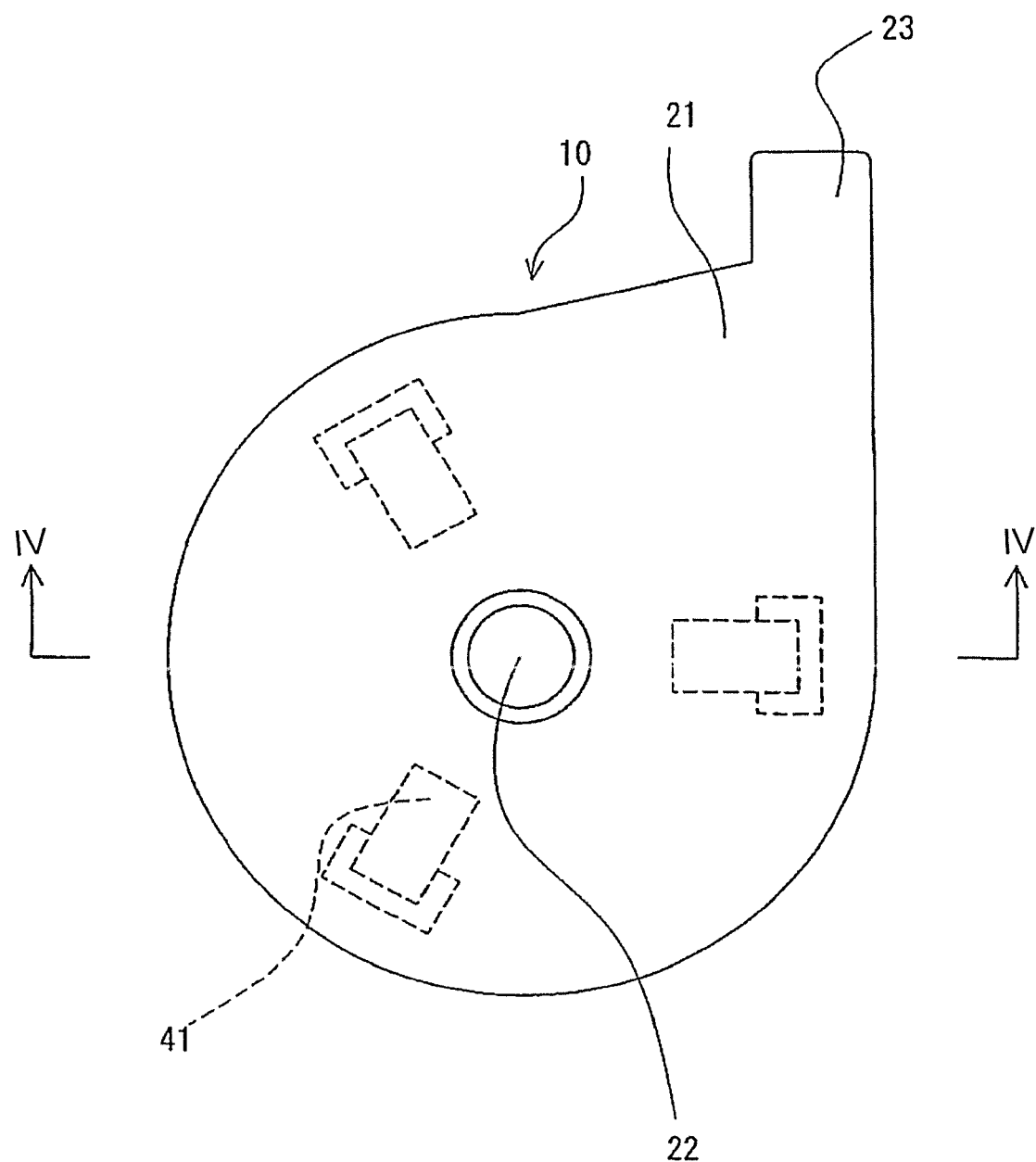
F I G. 3

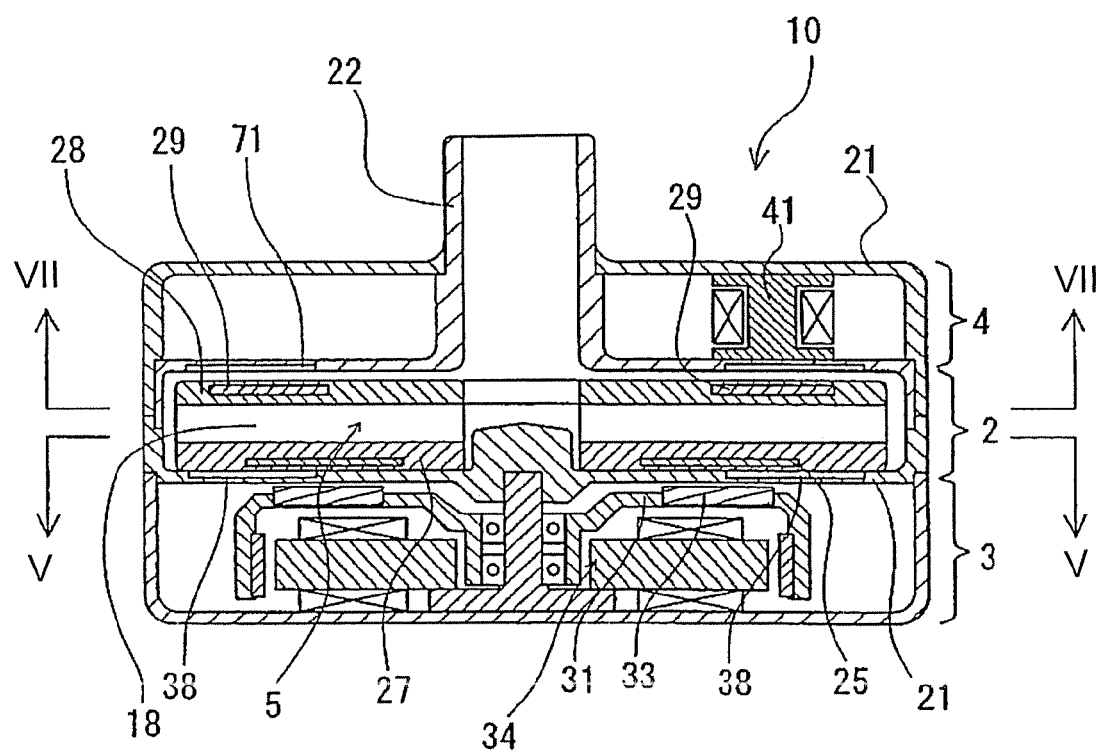
F I G. 4

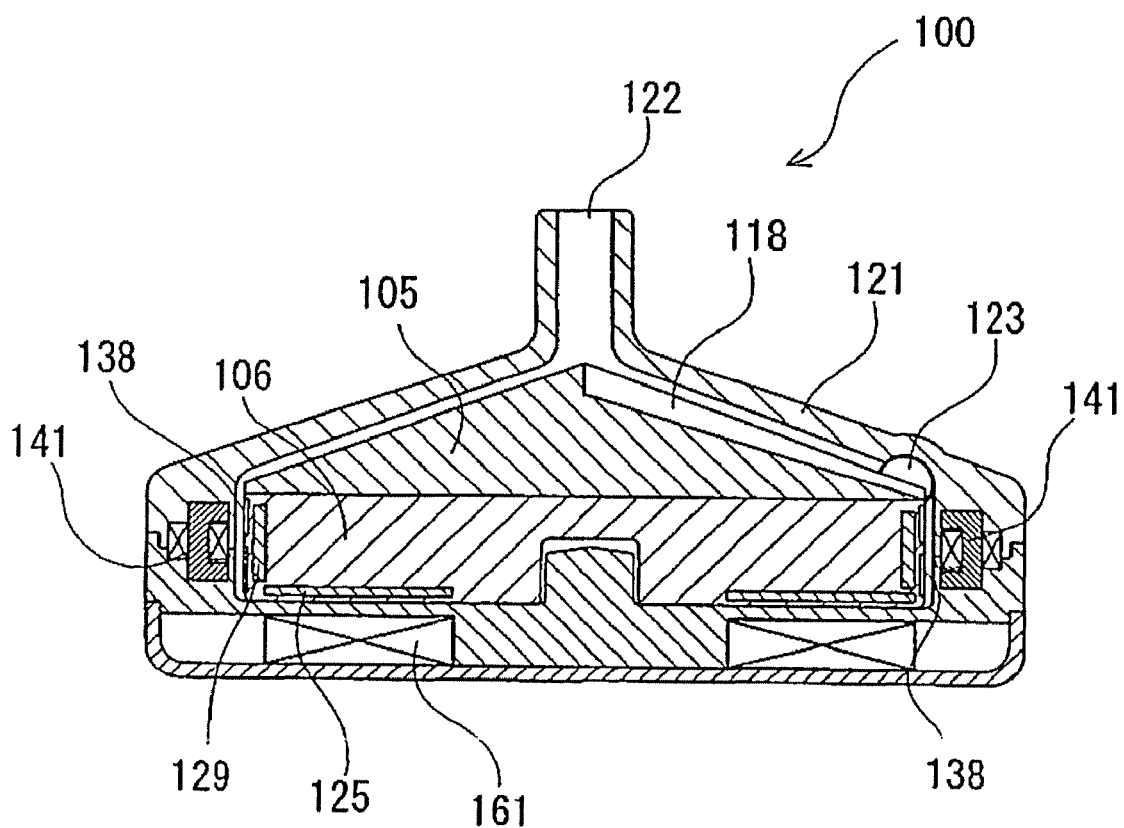
F I G. 1 4
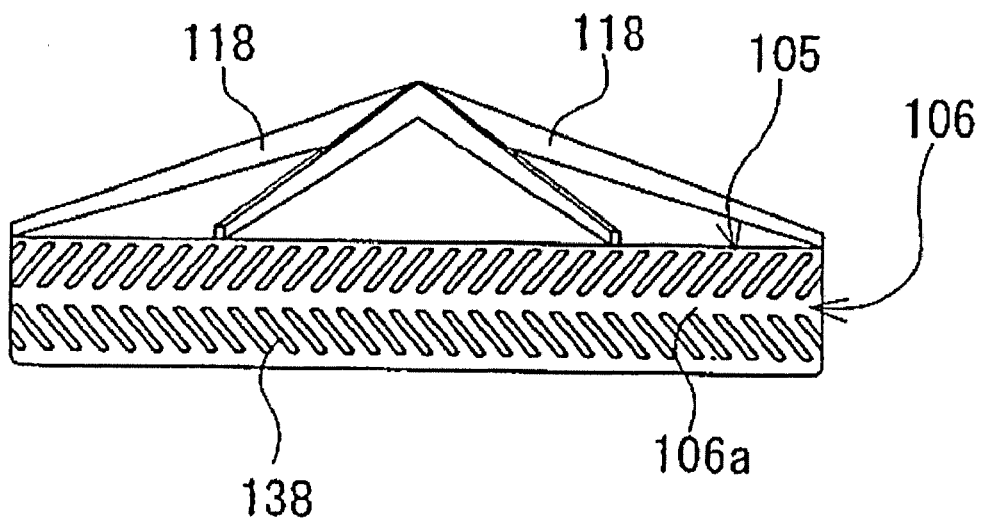
F I G. 1 5

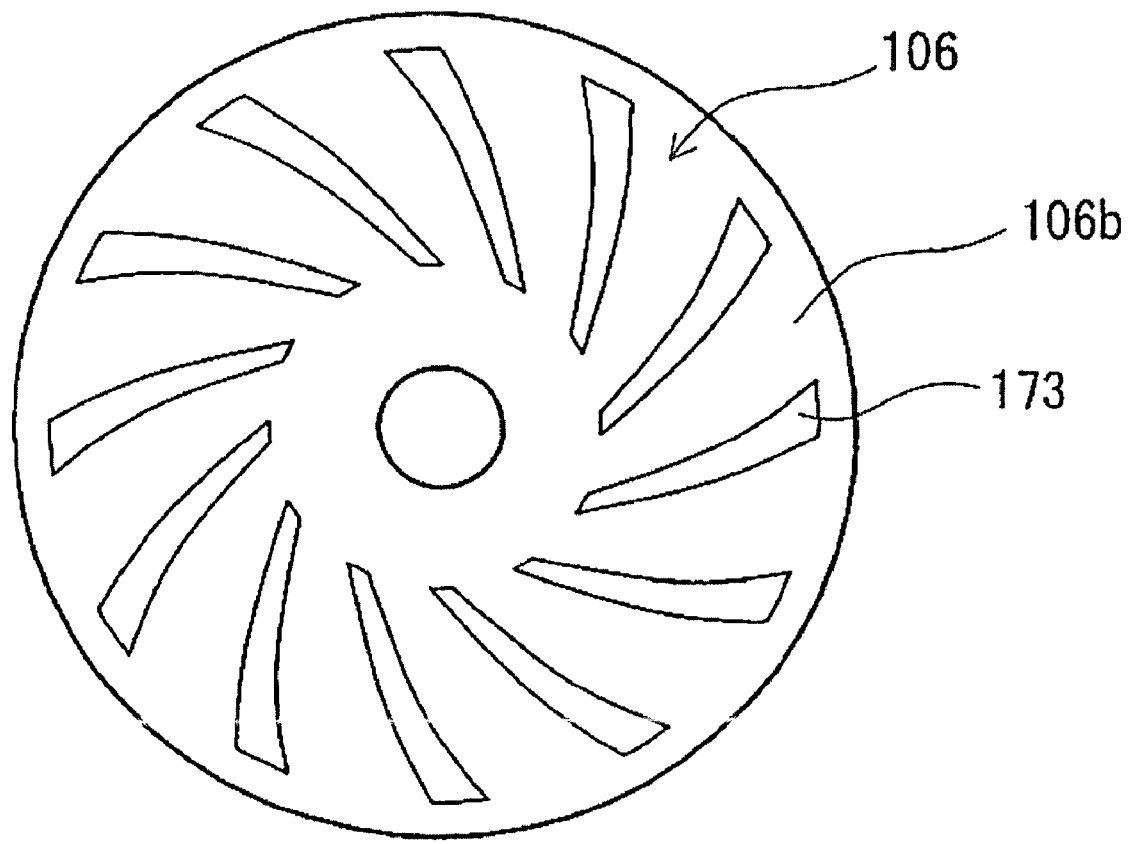
F I G. 1 6

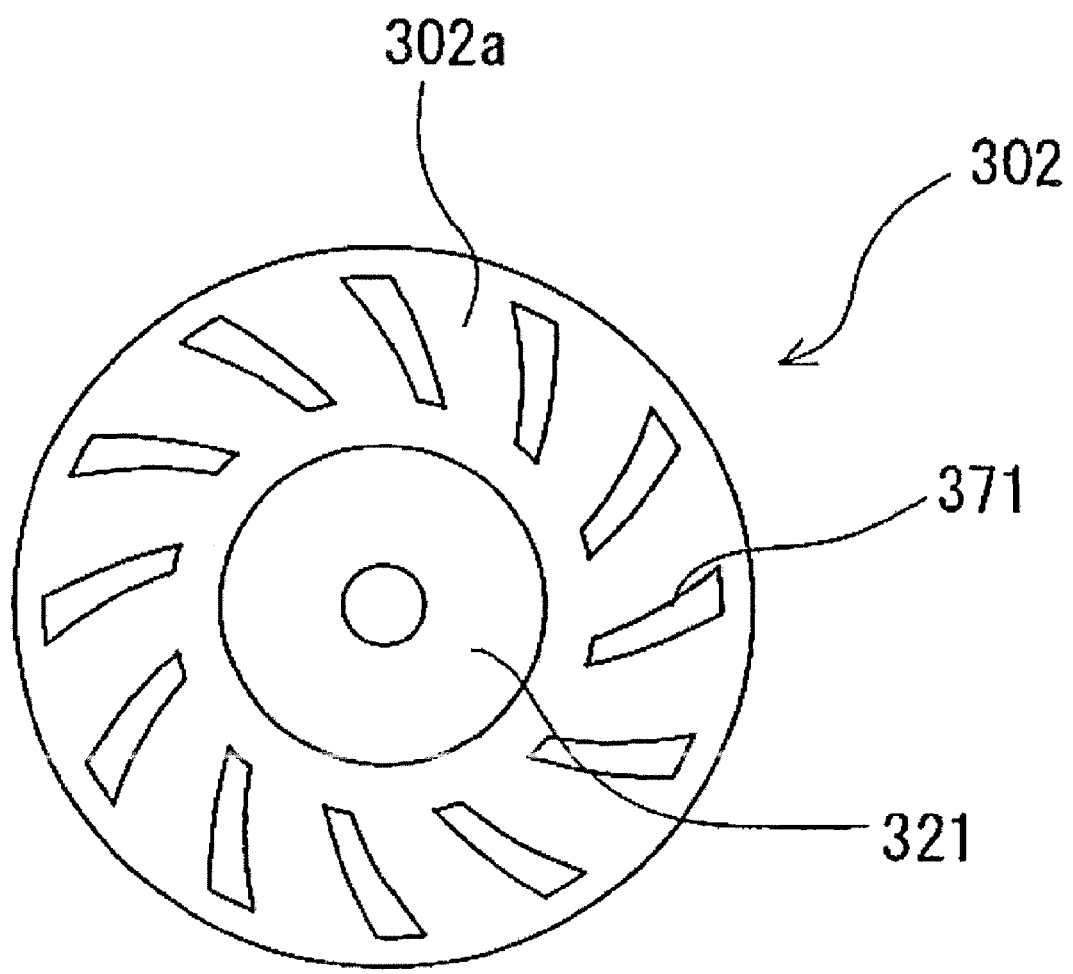
F I G. 2 2

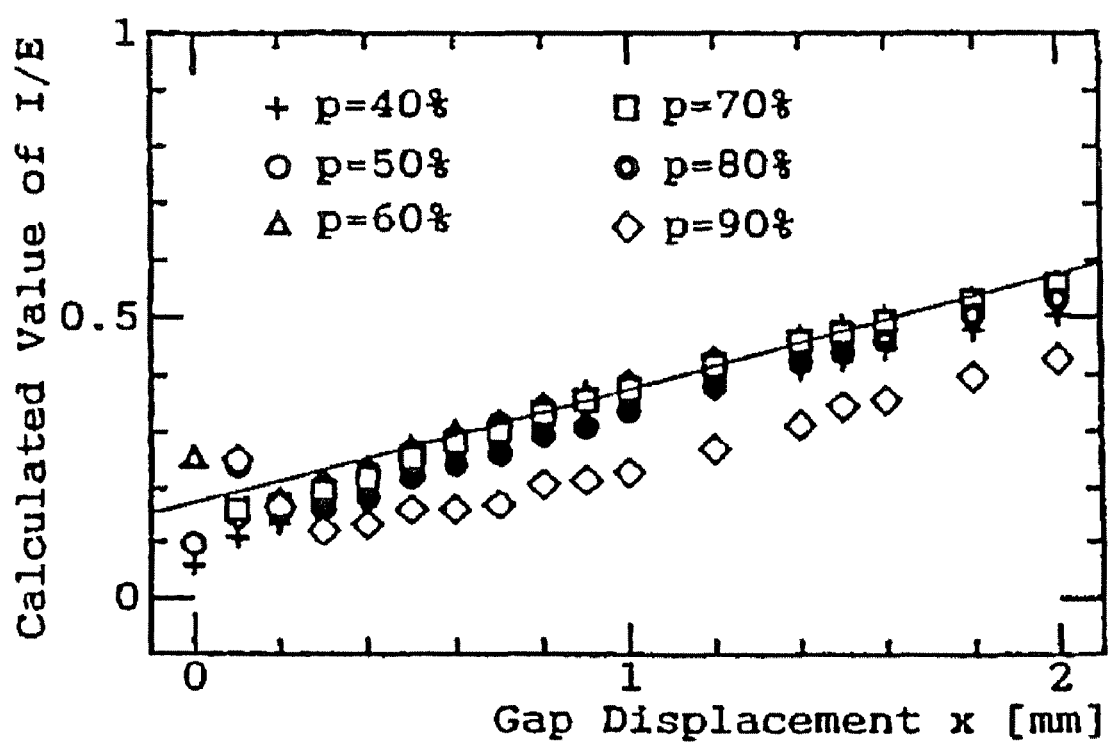
F I G. 2 5

SENSORLESS MAGNETIC BEARING TYPE BLOOD PUMP APPARATUS

TECHNOLOGICAL FIELD

The subject matter and invention described herein generally relate to a blood pump apparatus. More specifically, the disclosed subject matter and invention pertain to a sensorless magnetic bearing type blood pump apparatus for feeding a medical liquid such as blood.

BACKGROUND DISCUSSION

Recently, blood pumps have been used more and more frequently for extracorporeal blood circulation in pump-oxygenators. As a centrifugal pump, there have been used pumps of the system in which physical communication between the exterior and a blood chamber in the pump is completely excluded, whereby penetration of bacteria or the like can be prevented, and driving torque from an external motor is transmitted by use of magnetic coupling.

A centrifugal blood pump of this type has been proposed in Japanese Patent Laid-Open No. Hei 9-206372 (Patent Document 1) (corresponding to U.S. Pat. No. 5,947,703).

The centrifugal blood pump apparatus shown in this unexamined patent publication includes a housing having a blood inflow port and a blood outflow port, a centrifugal blood pump unit having an impeller which is rotated inside the housing and which feed a blood by a centrifugal force at the time of rotation, a non-control-type magnetic bearing component section (impeller rotational torque generating unit) for the impeller, and a control-type magnetic bearing component section (impeller position control unit) for the impeller, wherein the impeller is rotated in the state of being kept at a predetermined position inside the housing under the operations of the non-control-type magnetic bearing component section and the control-type magnetic bearing component section. Further, the impeller has a multiplicity of hydrodynamic grooves formed in the bottom surface (lower surface) thereof. The presence of the hydrodynamic grooves ensures that, although the impeller would be attracted toward the impeller rotational torque generating unit when the impeller position control unit is not operated (in other words, when the operation of electromagnets is stopped), the impeller is spaced, though only a little, from the inside surface of the housing and is rotated in a non-contact condition due to a hydrodynamic bearing effect produced between the hydrodynamic grooves and the inside surface of the housing.

The centrifugal blood pump apparatus of Patent Document 1 has effects which make the apparatus effective as a so-called magnetic levitation type pump apparatus. Hydrodynamic grooves provided in the pump apparatus are intended to act when impeller position control is stopped, i.e., when the operation of electromagnets for attracting the impeller is stopped, upon the occurrence of a trouble in the control type magnetic bearing component section (impeller position control unit) for the impeller. Thus, the hydrodynamic grooves are not utilized at the time of normal rotation. During rotation by use of the hydrodynamic grooves alone, especially in a low-rotating-speed condition, hemolysis or the like may occur. In addition, the magnetic levitation involves the need to provide an impeller position sensor, so that there are limitations with respect to reducing the size of the apparatus. Further, electric power is required for the magnetic levitation of the impeller.

On the other hand, the centrifugal blood pump apparatus 1 disclosed in Japanese Patent Laid-Open No. 2004-209240 (hereinafter referred to as Patent Document 2) (corresponding to U.S. Patent Application Publication No. 2004/209240) includes a centrifugal pump unit 2 having an impeller 21 which has first magnetic bodies 25 and is rotated inside a housing 20 so as to feed liquid by a centrifugal force at the time of rotation, a rotor 31 having magnets 33 for attracting the first magnetic bodies 25 of the impeller 21, an impeller rotational torque generating unit 3 having a motor 34 for rotating the rotor 31, and hydrodynamic grooves 38 provided in an inside surface, on the rotor 31 side, of the housing 21. The pump apparatus 1 has electromagnets 41 for assisting the levitation of the impeller 21 by attracting the impeller 21 in a direction opposite to the direction of attraction by the magnets 33 of the rotor 31. The centrifugal blood pump apparatus 1 includes a control mechanism, and the control mechanism has an impeller rotational torque generating unit current monitoring function. The control mechanism controls the electromagnets by use of the current detected by the impeller rotational torque generating unit current monitoring function.

The centrifugal blood pump apparatus 1 of Patent Document 2 eliminates the need for a position sensor, thereby enabling a reduction in the pump size. However, the apparatus in Patent Document 2 does not perform distance estimation related to the levitated position of the impeller, and the control limit controlling the setting of the distance between the impeller and the housing (on one side or the impeller rotational torque generating unit side) to limited to nearly about 0.1 mm. An attempt to increase the distance by increasing the attractive forces of the electromagnets may result in the impeller adhering to the electromagnet side in the presence of a tiny disturbance.

Research on PWM Type Self-sensing Magnetic Levitation (Proceedings of the 5th Symposium of Dynamics Related to Electromagnetic Force, pp. 547-552 (1993)), Kenichi Matsuda and Yoji Okada, (hereinafter referred to as Non-Patent Document 1) discloses a theory of magnetic levitation based on a PWM type self-sensing (in other words, sensorless) system. However, Non-Patent Document 1 discloses only the PWM type self-sensing magnetic levitation system, and does not disclose any specific configuration for applying it to a blood pump apparatus, such as the manner of addressing a troubled magnetic bearing or the like.

Accordingly, a need exists for a sensorless magnetic bearing type blood pump apparatus that is able to achieve sensorless control of the magnetically levitated condition of a rotating body in the condition where a certain distance is secured between the rotating body and a housing (on one side or the rotating body rotational torque generating unit side), while also being able to detect a troubled condition of the magnetic bearing such as a disturbance, and which makes it possible to achieve a transition (change-over) to a hydrodynamic bearing mode upon detection of a trouble in the magnetic bearing mode, and return to the magnetic bearing mode upon dissolution of the trouble.

SUMMARY

A sensorless magnetic bearing type blood pump apparatus comprises a blood pump and a control mechanism for controlling the blood pump. The blood pump includes: a housing having a liquid inflow port and a liquid outflow port; a pump unit provided therein with a first magnetic body and rotated in the housing so as to feed a liquid; a rotating body rotational torque generating unit for attracting the first magnetic body of the rotating body of the pump unit and for rotating the rotating body; a rotating body magnetic bearing unit for magnetically attracting the rotating body in a direction different from the direction of attraction of the rotating body by the rotating body rotational torque generating unit and for permitting the rotating body to be rotated in a non-contact condition in the housing; and a hydrodynamic bearing section provided in an inside surface of the housing on the rotating body rotational torque generating unit side, or in a surface of the rotating body on the rotating body rotational torque generating unit side to permit the rotating body to be rotated in a non-contact condition in the housing when the operation of the rotating body magnetic bearing unit is stopped. The blood pump does not include any sensors for measuring the position of the rotating body. The rotating body magnetic bearing unit includes an electromagnet for attracting the first magnetic body or a second magnetic body provided separately from the first magnetic body, in the rotating body. The control mechanism includes: a pulse width modulation type electromagnet driving unit which drives the electromagnet; a carrier component measuring unit which measures carrier components of the voltage and current in the pulse width modulation type electromagnet driving unit; rotating body position data and modulation factor calculating units which respectively calculate rotating body position data and the modulation factor of a pulse width modulated waveform by use of carrier wave data measured by the carrier component measuring unit; a rotating body position controlling means for controlling the pulse width modulation type electromagnet driving unit by utilizing the rotating body position data calculated by the rotating body position data calculating unit; and a bearing mode changing-over means for effecting change-over to a hydrodynamic bearing mode by stopping the driving of the pulse width modulation type electromagnet driving unit when the modulation factor calculated by the modulation factor calculating function is outside a predetermined range and for restarting the driving of the pulse width modulation type electromagnet driving unit, thereby returning to a magnetic bearing mode, upon confirmation of satisfaction of predetermined conditions after the change-over to the dynamic pressure driving mode.

In the sensorless magnetic bearing type blood pump apparatus as above, preferably, the hydrodynamic bearing section is included of hydrodynamic grooves or a deformed surface provided in an inside surface, on the rotating body rotational torque generating unit side, of the housing or in a surface, on the rotating body rotational torque generating unit side, of the rotating body.

Or, preferably, the hydrodynamic bearing section is included of hydrodynamic grooves or a deformed surface provided in a surface, on the rotating body magnetic bearing unit side, of the rotating body or an inside surface, facing the surface of the rotating body, of the housing.

In the sensorless magnetic bearing type blood pump apparatus, preferably, the blood pump has second hydrodynamic grooves provided in an inside surface, on the rotating body magnetic bearing unit side, of the housing or in a surface, on the rotating body magnetic bearing unit side, of the rotating body.

Also, preferably, the carrier component measuring unit includes a voltage resonant circuit, a voltage wave detection circuit, a current resonant circuit, and a current wave detection circuit.

In the sensorless magnetic bearing type blood pump apparatus, preferably, the control mechanism stores a predetermined modulation factor range, and the bearing mode changing-over function is for effecting change-over to the hydrodynamic bearing mode by stopping the driving of the pulse width modulation type electromagnet driving unit when a modulation factor outside the predetermined modulation factor range is calculated by the modulation factor calculating function.

Also, preferably, the control mechanism has a rotating body rotational torque generating unit current monitoring function, and the bearing mode changing-over function stores a predetermined rotating body rotational torque generating unit current range, and is for effecting return to the magnetic bearing mode by judging that the predetermined conditions are satisfied when a rotating body rotational torque generating unit current within the rotating body rotational torque generating unit current range is detected by the rotating body rotational torque generating unit current monitoring function.

Or, preferably, the bearing mode changing-over function is for effecting return to the magnetic bearing mode by judging that the predetermined conditions are satisfied when the lapse of a predetermined time is detected after the change-over to the hydrodynamic bearing mode.

Also, preferably, the rotating body rotational torque generating unit includes a rotor having a magnet for attracting the first magnetic body of the rotating body, and a motor for rotating the rotor.

Preferably, the rotating body rotational torque generating unit includes a plurality of stator coils arranged on the circumference of a circle for attracting the first magnetic body of the rotating body and rotating the rotating body.

In the sensorless magnetic bearing type blood pump apparatus as above, preferably, the blood pump is a centrifugal blood pump or an axial flow blood pump.

The blood pump apparatus according to the present invention has no position sensor. Thus, the apparatus can be reduced in size and is relatively low in power consumption. Further, in the blood pump apparatus, the driving of the electromagnet for attracting the rotating body is conducted by the pulse width modulation type electromagnet driving unit, and the apparatus includes the rotating body position data calculating function and the modulation factor calculating function for respectively calculating rotating body position data and the modulation factor of a pulse width modulated waveform, by use of carrier wave data on the voltage and current in the pulse width modulation type electromagnet driving unit. Since position control for the rotating body (control of the pulse width modulation type electromagnet driving unit) is conducted by the rotating body position data obtained in this manner, it is possible to achieve a control in the condition where a certain distance is secured between the rotating body and the housing, so that a good control of the rotating body can be realized. Furthermore, a trouble about the rotating body can be detected from the calculated modulation factor, transition (change-over) from the magnetic bearing mode to the hydrodynamic bearing mode can be performed upon a trouble about the rotating body, and, thereafter, return from the hydrodynamic bearing mode to the magnetic bearing mode can also be performed. Therefore, it is possible to perform a magnetic bearing control in normal conditions, to maintain the rotation of the rotating body in the hydrodynamic bearing mode in emergency, and to effect returning to the rotation of the rotating body in the magnetic bearing mode, so that a good control of rotation of the rotating body can be achieved in a sensorless system.

Another aspect involves a method for controlling operation of a sensorless magnetic bearing type blood pump apparatus, wherein the sensorless magnetic bearing type blood pump apparatus comprises a blood pump comprised of a housing having a liquid inflow port and a liquid outflow port, and a rotatable body rotatably positioned in the housing to feed liquid and provided with an electromagnet. The method comprises rotating the rotatable body in a non-contact condition in the housing in a magnetic bearing mode through operation of a pulse width modulation type electromagnet driving unit which drives the electromagnet, measuring carrier components of voltage and current in the pulse width modulation type electromagnet driving unit to obtain carrier wave data, and calculating a modulation factor of a pulse width modulated waveform using the carrier wave data. The method also involves changing-over from the magnetic bearing mode to a hydrodynamic bearing mode by stopping driving of the pulse width modulation type electromagnet driving unit when the modulation factor is outside a predetermined range and rotating the rotatable body in a non-contact condition in the housing through use of a hydrodynamic bearing section of the blood pump, and restarting the driving of the pulse width modulation type electromagnet driving unit to return to the magnetic bearing mode upon satisfying predetermined conditions after the change-over to the hydrodynamic bearing mode.

BRIEF DESCRIPTION OF THE DRAWING FIGURES

FIG. 3 is a plan view of the blood pump shown in FIG. 2;

FIG. 4 is a cross-sectional view of the blood pump taken along the section line IV-IV in FIG. 3.

FIG. 14 is a cross-sectional view of the blood pump shown in FIG. 13 taken along the section line XIV-XIV in FIG. 13.

FIG. 15 is a front view of a rotor with rotating body used in the blood pump shown in FIG. 14.

FIG. 16 is a bottom view of the rotor with rotating body shown in FIG. 15.

FIG. 22 is a bottom view of the rotating body used in the blood pump shown in FIG. 20.

FIG. 25 is a diagram showing experimental results for the sensorless type magnetic levitation system shown in Non-Patent Document 1.

DETAILED DESCRIPTION

Figure 1:
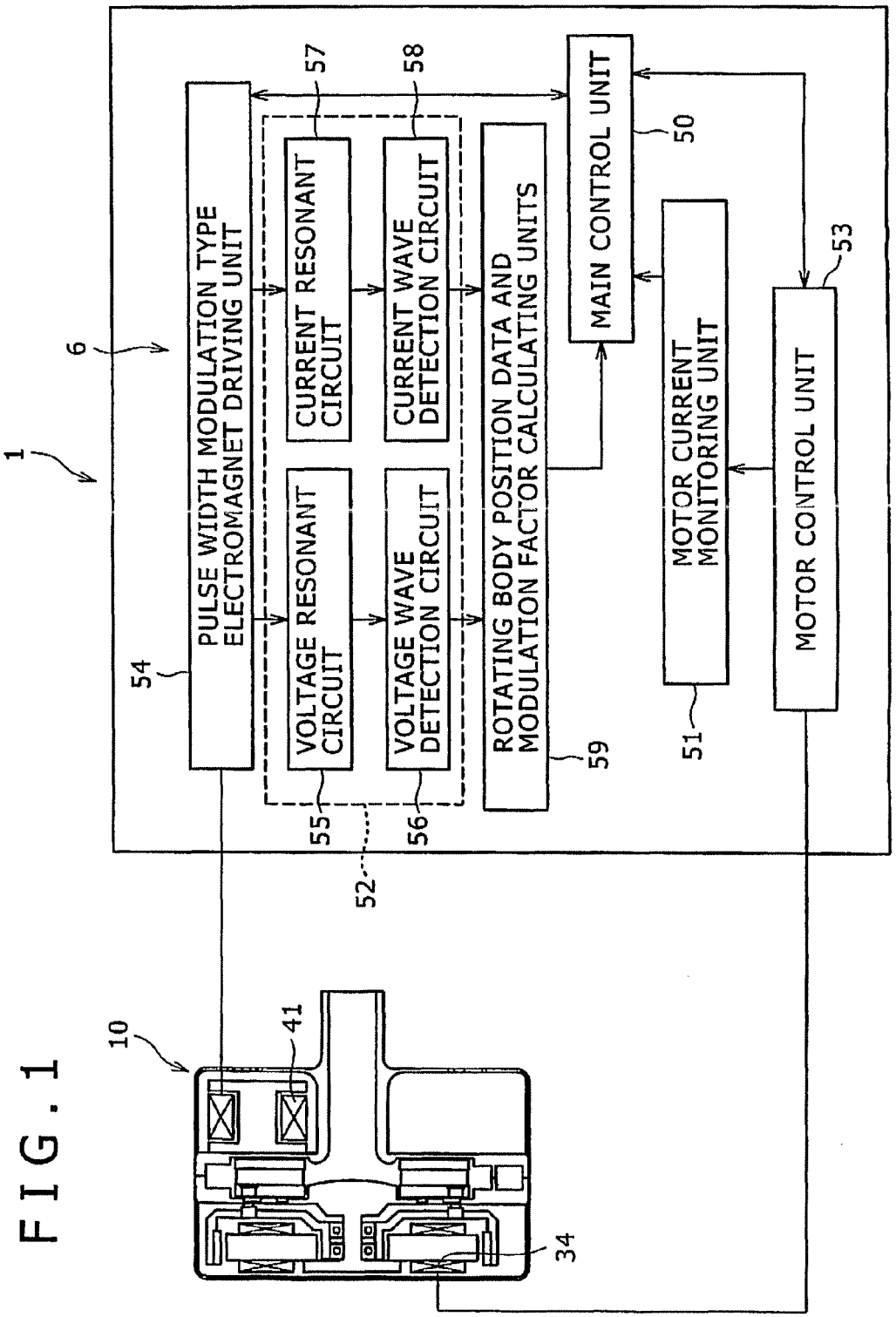
FIG. 1 is a block diagram of an embodiment including a control mechanism of a sensorless magnetic bearing type blood pump apparatus as disclosed herein.

The sensorless magnetic bearing type blood pump apparatus disclosed herein is described in detail below with reference to embodiments shown in the drawings.

As generally illustrated in FIG. 1, the sensorless magnetic bearing type blood pump apparatus 1 disclosed herein includes a blood pump 10 and a control mechanism 6 for controlling the blood pump 10.

FIGS. 1-4 illustrate that the blood pump 10 includes: a housing 21 having a liquid inflow port 22 and a liquid outflow port 23; a pump unit 2 having a rotating or rotatable body 5 provided therein with first magnetic bodies 25, rotated in the housing 21, and feeding a liquid by a centrifugal force at the time of rotation; a rotating body rotational torque generating unit 3 for attracting the first magnetic bodies 25 of the rotating body 5 of the pump unit 2 and rotating the rotating body 5; a rotating body magnetic bearing unit 4 for magnetically attracting the rotating body 5 in a direction different from (opposite to) the direction of attraction of the rotating body 5 by the rotating body rotational torque generating unit 3, and permitting the rotation of the rotating body 5 in a non-contact condition in the housing 21; and a hydrodynamic bearing section 38 provided in the housing inside surface on the rotating body rotational torque generating unit 3 side or in a surface of the rotating body 5 on the rotating body rotational torque generating unit 3 side, and permitting the rotation of the rotating body 5 in a non-contact condition in the housing 21 at the time when the operation of the rotating body magnetic bearing unit 4 is stopped, and does not include any sensor for measurement of the position of the rotating body 5. The rotating body magnetic bearing unit 4 has an electromagnet 41 for attracting the first magnetic bodies 25 or second magnetic bodies 29, provided separately from the first magnetic bodies 25, of the rotating body 5.

The control mechanism 6 includes: a pulse width modulation electromagnet driving unit (PWM type electromagnet driving unit) 54 for driving the electromagnet 41; a carrier component measuring unit 52 (55, 56, 57, 58) for measuring carrier components of the voltage and current in the PWM type electromagnet driving unit 54; rotating body position data and modulation factor calculating units for respectively calculating rotating body position data and the modulation factor of a pulse width modulated waveform, by utilizing the carrier wave data measured by the carrier component measuring unit 52; a rotating body position controlling means for controlling the PWM type electromagnet driving unit 54 by utilizing the rotating body position data calculated by the rotating body position data calculating unit; and a bearing mode changing-over means for effecting transfer or changeover from the magnetic bearing mode to a hydrodynamic bearing mode by stopping the driving of the PWM type electromagnet driving unit 54 when the modulation factor calculated by the modulation factor calculating unit is outside a predetermined range, and restarting the driving of the PWM type electromagnet driving unit 4 upon confirmation of satisfaction of predetermined conditions after the transfer to the hydrodynamic bearing mode to achieve a return to the magnetic bearing mode.

As shown in FIGS. 1 to 7, the blood pump apparatus 1 in this embodiment includes the housing 21 having the blood inflow port 22 and the blood outflow port 23, the blood pump unit 2 having an impeller 5 serving as the rotating body which rotates in the housing 21 and feeds blood by centrifugal force at the time of rotation, an impeller rotational torque generating unit (non-control type magnetic bearing constituting unit) 3 for the impeller 5, and an impeller position control unit (control type magnetic bearing constituting unit) 4 for the impeller 5.

In the blood pump 10 as shown in FIG. 4, the impeller rotational torque generating unit 3 includes a rotor 31 contained in the blood pump 10, and a motor 34 for rotating the rotor 31. The rotor 31 has a plurality of permanent magnets 33 provided at a surface on the blood pump unit 2 side. The center of the rotor 31 is fixed to a rotating shaft of the motor 34. A plurality of the permanent magnets 33 are provided at spaced apart positions at equal or regular angular intervals so as to correspond to the layout form (the number and the layout positions) of the permanent magnets 25 of the impeller 5.

In addition, a magnetic bearing mechanism in the blood pump 10 is comprised of the second magnetic bodies 29 provided at an upper shroud of the impeller 5 and the electromagnet 41 which attracts the second magnetic bodies 29 of the impeller 5 in a direction opposite the side of the impeller rotational torque generating unit 3.

As shown in FIG. 4, the impeller 5 is held at a predetermined position in the housing 21 by the actions of the non-control type magnetic bearing constituting unit 3 and the control type magnetic bearing constituting unit 4, and is normally rotated without making contact with the inside surface of the housing 21.

The blood pump 10 includes the electromagnets 41 for attracting the impeller 5 (specifically, the electromagnets 41 attract the second magnetic bodies 29 provided in the impeller 5), but does not have any position sensors for detecting the position of the rotating body.

In the pump apparatus 1 according to this embodiment, the blood pump unit 2 is comprised of the housing 21 and the impeller 5 contained in the housing 21.

Figure 2:
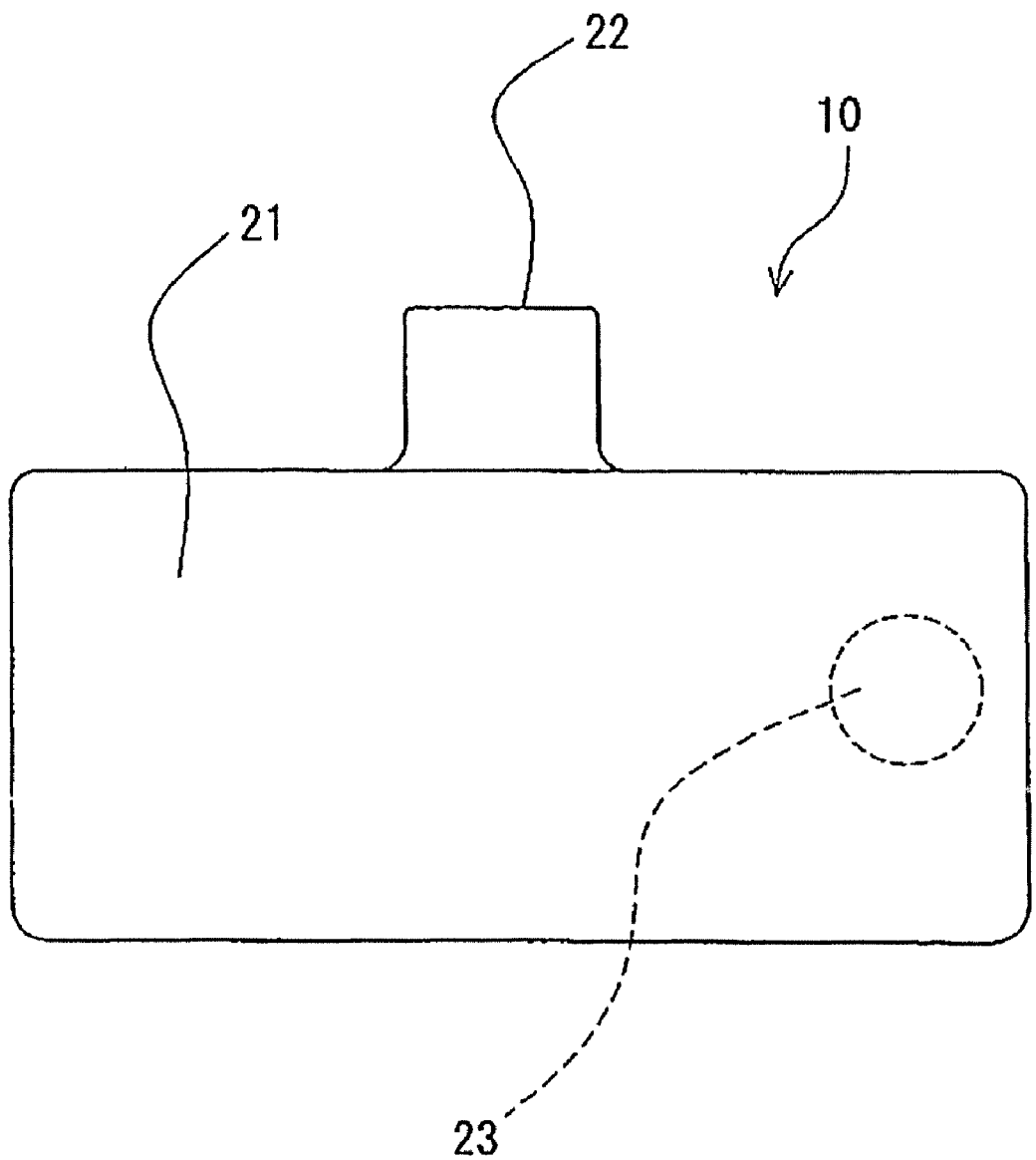
FIG. 2 is a front view of an example of a blood pump used in the sensorless magnetic bearing type blood pump apparatus disclosed herein.

The housing 21 which includes the blood inflow port 22 and the blood outflow port 23 is formed from a non-magnetic material. In the housing 21, a blood chamber is formed which communicates with the blood inflow port 22 and the blood outflow port 23. The impeller 5 is contained in the housing 21. The blood inflow port 22 projects from the vicinity of the center of the upper surface of the housing 21. Though not shown, the blood inflow port 22 is composed of a bent pipe. The blood outflow port 23 projects in a tangential direction from the side surface of the housing 21 and is formed in a roughly hollow cylindrical shape as shown in FIGS. 2 and 3.

Figure 5:
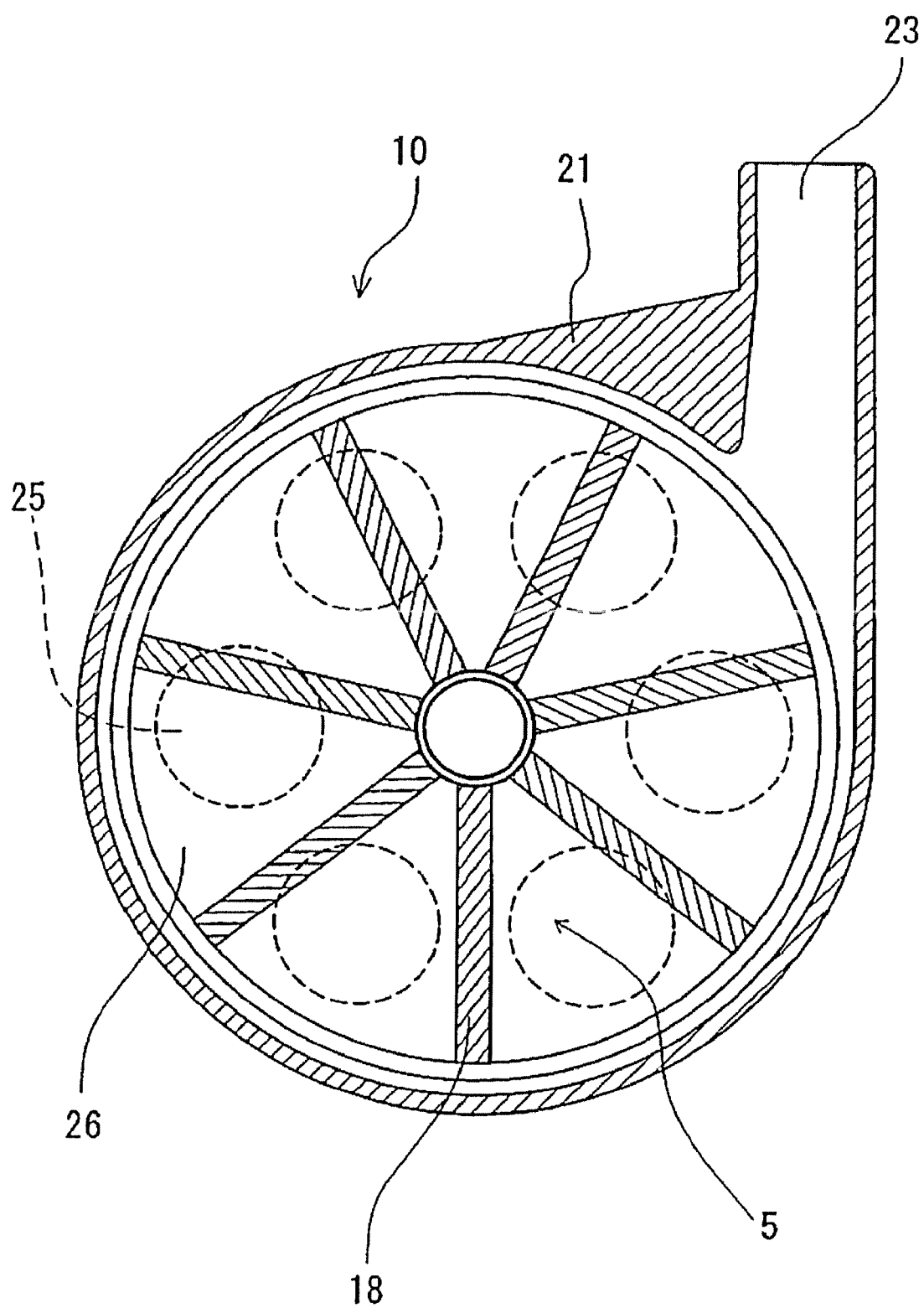
FIG. 5 is a cross-sectional view of the blood pump taken along the section line V-V in FIG. 4.

As shown in FIG. 4, the circular disk-like impeller 5 having a through-hole in its center is contained in the blood chamber formed inside the housing 21. As shown in FIGS. 4 and 5, the impeller 5 includes an annular plate-like member (lower shroud) 27 forming a lower surface of the impeller 5, an annular plate-like member (upper shroud) 28 having an opening in its center and forming an upper surface of the impeller 5, and a plurality of (for example, seven) vanes 18 formed between the annular plate-like members (shrouds) 27 and 28. A plurality of (seven) blood passages 26 each partitioned by the adjacent vanes 18 are formed between the lower shroud and the upper shroud. As shown in FIG. 5, each of the blood passages communicates with the central opening of the impeller 5, and extends from the central opening of the impeller 5 toward the outer peripheral edge of the impeller 5 in such a manner that the passages gradually increase in width. In other words, the vanes 18 are each formed between the adjacent blood passages. In this embodiment, the blood passages and the vanes 18 are provided respectively at regular angular intervals and in substantially the same shape.

As shown in FIG. 5, a plurality of (for example, six) magnetic bodies 25 (permanent magnets, driven magnets) are embedded in the impeller 5. In this embodiment, the magnetic bodies 25 are embedded in the lower shroud 27. The magnetic bodies 25 (permanent magnets) thus embedded attract the impeller 5 toward the side opposite the blood inflow port 22 by the impeller rotational torque generating unit 3 (described later) and transmit a rotational torque from the impeller rotational torque generating unit 3.

In addition, the upper shroud of the impeller 5 is itself magnetic or the upper shroud has magnetic members provided or mounted therein. In this embodiment, second magnetic bodies 29 are embedded in the upper shroud 28. The second magnetic bodies 29 attract the impeller 5 toward the side of the blood inflow port 22 by the electromagnets 41 in the impeller position control unit (described later). Magnetic stainless steel or the like can be used as the second magnetic bodies 29.

The impeller position control unit 4 and the impeller rotational torque generating unit 3 constitute the non-contact type magnetic bearing. The impeller 5 is pulled or attracted in opposite directions by the two units, whereby the impeller 5 is stabilized at an appropriate position in which it does not make contact with the inside surface of the housing 21, and is rotated in a non-contact condition in the housing 21.

As shown in FIGS. 3 and 4, the non-contact type bearing mechanism (impeller position control unit) 4 is comprised of a plurality of the electromagnets 41 fixed in position to attract the second magnetic bodies 29 of the impeller 5. The plurality of electromagnets 41 are spaced apart and positioned at equal or regular angular intervals. Each of the electromagnets 41 is composed of an iron core and a coil. In this embodiment, three electromagnets 41 are provided. However, the number of the electromagnets 41 may be more than three, for example four electromagnets may be used. By providing not less than three electromagnets 41 and controlling the electromagnetic forces thereof, it is possible to balance the forces exerted in the rotational axis (z-axis) direction of the impeller 5, and to control the moments about the x-axis and y-axis which are orthogonal to the rotational axis (z-axis).

Figure 6:
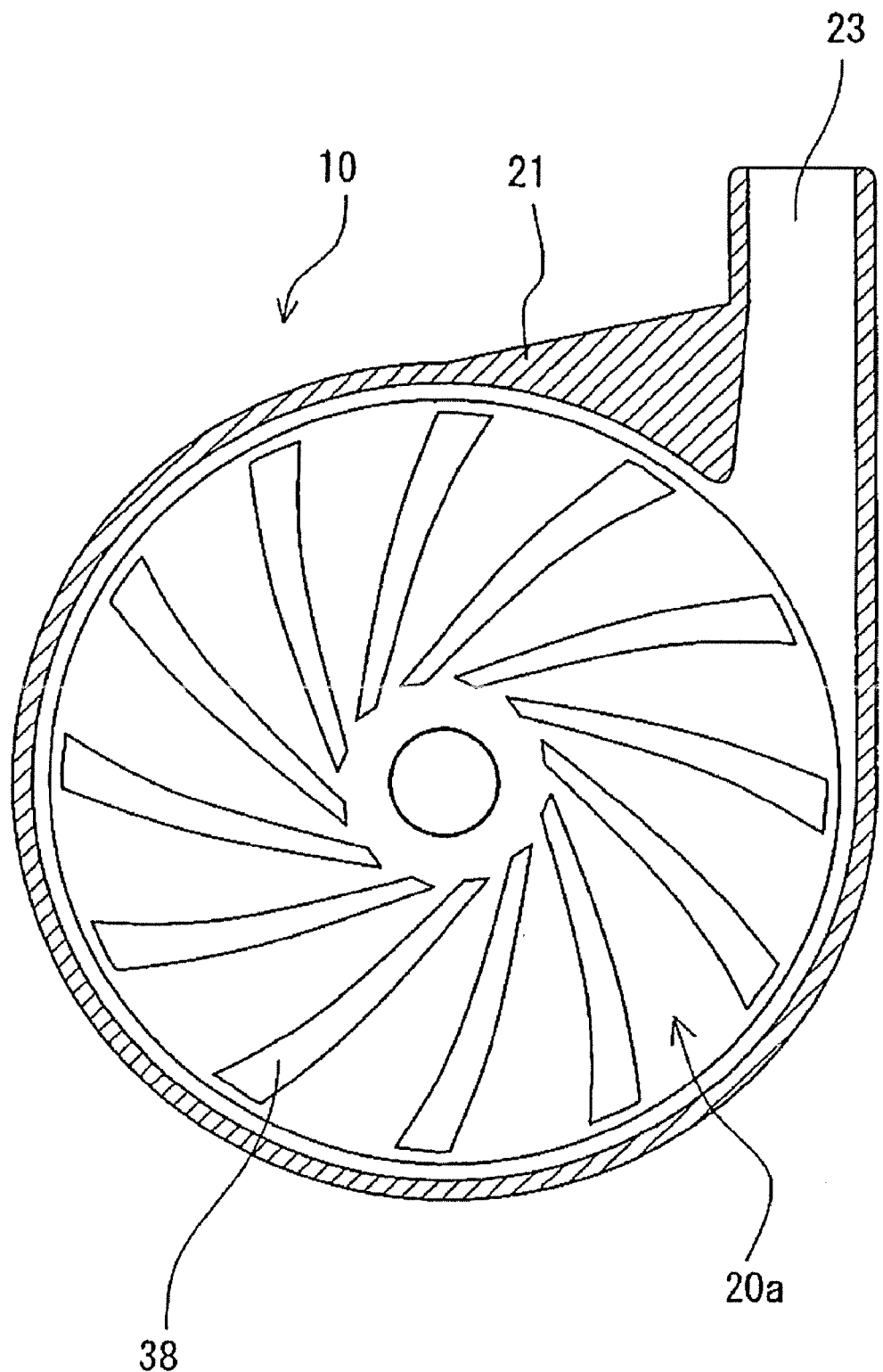
FIG. 6 is a cross-sectional view showing the condition where a rotating body is removed from the section along the section line V-V of the blood pump apparatus shown in FIG. 4.

As shown in FIG. 6, in this embodiment of the blood pump 10, the inside surface 21a of the housing containing the impeller 5 and defining the blood chamber, on the motor side 34, is provided with hydrodynamic grooves 38. The hydrodynamic grooves 38 constitute a hydrodynamic bearing section permitting rotation of the rotating body in a non-contact condition in the housing 21 when the operation of the rotating body magnetic bearing unit 4 is stopped.

Owing to a hydrodynamic bearing effect generated between the hydrodynamic grooves 38 and the impeller 5 by the rotation of the impeller 5 at a rotating speed not less than a predetermined speed, the impeller 5 is rotated in the non-contact condition.

As shown in FIG. 6, the hydrodynamic grooves 38 are formed in a size corresponding to the bottom surface (rotor side surface) of the impeller 5. In the pump apparatus 1 in this embodiment, each of the hydrodynamic grooves 38 has one end on an inner peripheral edge (circumference) of a circular portion slightly spaced from the center of the housing inside surface 20a, and extends therefrom to the vicinity of the outer edge of the housing inside surface 20a in a spiral form (in other words, in a bent or curved form/shape) while being gradually increased in width. The hydrodynamic grooves 38 are provided as a plurality of grooves. The individual hydrodynamic grooves 38 are substantially the same in shape with respect to each other and are laid out at substantially regular or equal intervals. The hydrodynamic grooves 38 are recesses having a depth of preferably about 0.005 to 0.4 mm. Preferably, the number of hydrodynamic grooves is about 6 to 36.

When the magnetic bearing is stopped, the rotating body would be attracted toward the impeller rotational torque generating unit 3. However, due to the presence of the hydrodynamic grooves 38, the rotating body is separated, though only slightly, from the housing inside surface by the hydrodynamic bearing effect formed between the hydrodynamic grooves 38 of the housing and the bottom surface of the impeller 5, and is rotated in a non-contact condition so as to secure a blood passage between the lower surface of the rotating body and the housing inside surface, so that stagnation of blood therebetween and the resultant generation of thrombus are prevented from occurring. Further, in a normal condition, the hydrodynamic grooves exhibit a stirring action between the lower surface of the rotating body and the housing inside surface so that partial blood stagnation therebetween is prevented from occurring.

Figure 7:
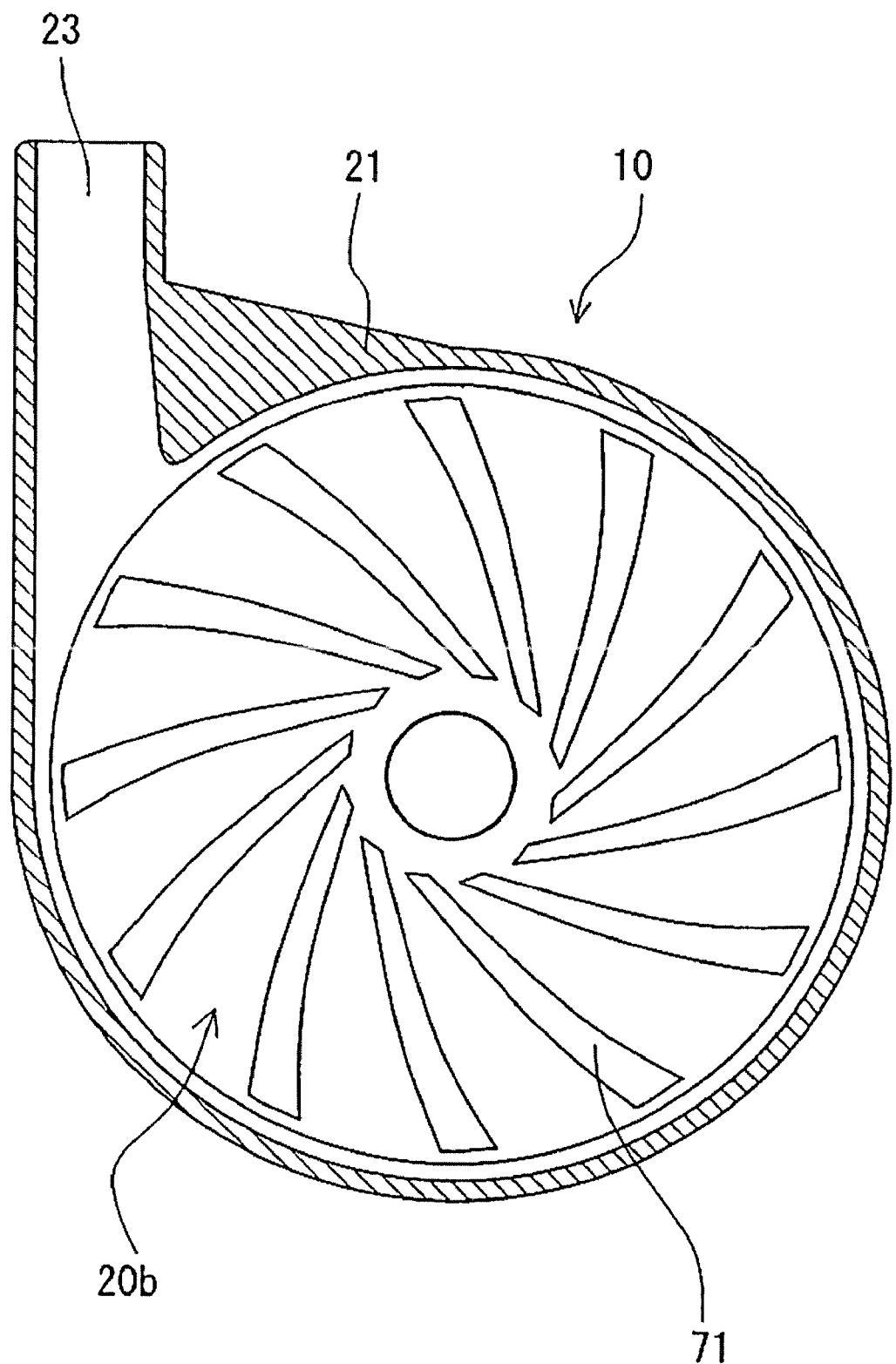
FIG. 7 is a cross-sectional view of the blood pump taken along the section line VII-VII in FIG. 4.

Furthermore, the apparatus preferably also comprises second hydrodynamic grooves 71 formed in a housing inside surface 20b on the electromagnet 41 side as shown in FIG. 7. The second hydrodynamic grooves 71 prevent the rotating body from adhering onto the housing inside surface 20b side when an external shock is exerted or when the dynamic pressure generated by the hydrodynamic grooves 38 becomes excessive.

Like the hydrodynamic grooves 38, the second hydrodynamic grooves 71 are formed in a size corresponding to the upper surface (the electromagnet side surface) of the impeller 5. In the blood pump 10 according to this embodiment, each of the hydrodynamic grooves 71 has one end on the peripheral edge (circumference) slightly spaced from the center of the housing inside surface 20b and extends in a spiral form (in other words, in a bent or curved form/shape) therefrom to the vicinity of the outer edge of the housing inside surface 20b while gradually increasing in width. In addition, the second hydrodynamic grooves 71 are provided plural in number, with each of the individual second hydrodynamic grooves 71 being substantially the same in shape and arranged at substantially equal or regular intervals. The hydrodynamic grooves 71 are recesses having a depth of preferably about 0.005 to 0.4 mm. The number of hydrodynamic grooves is about 6 to 36. In this embodiment, 12 hydrodynamic grooves are arranged at an equal angular intervals relative to the center axis of the rotating body.

The second hydrodynamic grooves may be provided in a surface, not on the housing side but on the electromagnet side, of the impeller 5. In that case, also, the second hydrodynamic grooves are configured in the same manner as those mentioned above.

The second hydrodynamic grooves are preferably formed on the housing side. This permits the hydrodynamic grooves to be formed relatively easily. Furthermore, the rotating body can be made smaller in thickness and weight, as compared with the case where the rotating body is provided with the hydrodynamic grooves. The thinner and lighter-weight rotating body will exhibit a relatively high disturbance resistance.

Figure 8:
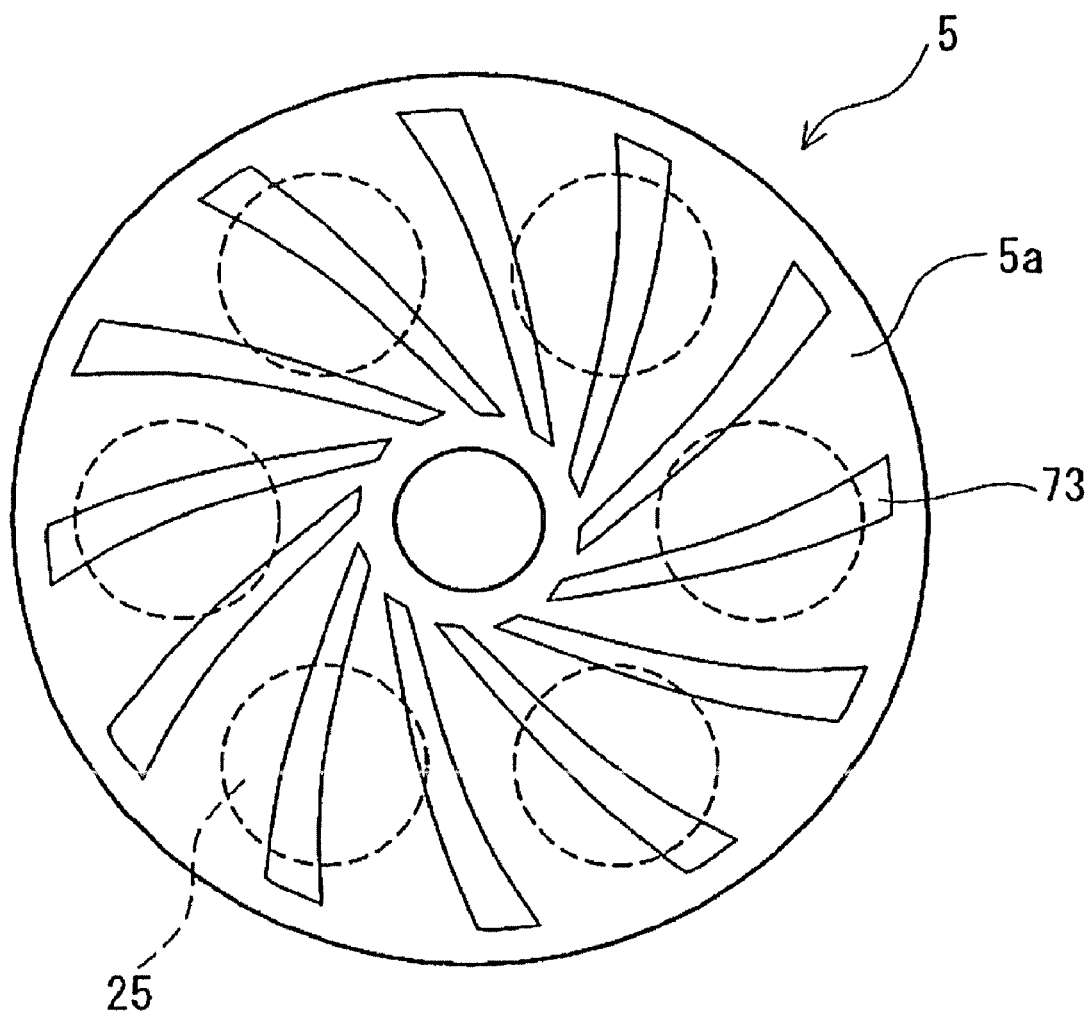
FIG. 8 is a bottom view of a rotating body used in a sensorless magnetic bearing type blood pump apparatus according to another disclosed embodiment.

The hydrodynamic bearing section is not limited to the above-mentioned hydrodynamic grooves 38. For example, the hydrodynamic bearing section may be comprised of hydrodynamic grooves 73 provided in a surface 5a, on the side of the impeller rotational torque generating unit 3, of the impeller 5, as shown in FIG. 8. The hydrodynamic grooves 73 possess the same configuration as that described with respect to the hydrodynamic grooves 38.

In addition, the hydrodynamic bearing section may be formed by a deformed surface (or specially shaped surface) provided in one of the inside surface, on the side of the impeller rotational torque generating unit 3, of the housing 21 and a surface, opposed to this inside surface, of the impeller 5. As the deformed surface, a relative sliding surface shape of a sliding bearing can be utilized. Preferred examples of the relative sliding surface shape of a sliding bearing include a slant plane bearing and a tapered land bearing.

As mentioned above, the sensorless magnetic bearing type blood pump apparatus includes the control mechanism 6 which comprises: the PWM type electromagnet driving unit 54 for driving the electromagnets 41; the carrier component measuring unit 52 (55, 56, 57, 58) for measuring carrier components of the voltage and current in the PWM type electromagnet driving unit 54; rotating body position data and modulation factor calculating units for respectively calculating rotating body position data and the modulation factor of a pulse width modulated waveform, by use of carrier wave data measured by the carrier component measuring unit 52 (55, 56, 57, 58); rotating body position control means for controlling the PWM type electromagnet driving unit 54 by utilizing the rotating body position data calculated by the rotating body position data calculating unit; and bearing mode changing-over means for achieving transfer or changeover to a hydrodynamic bearing mode by stopping the driving of the PWM type electromagnet driving unit 54 when the modulation factor calculated by the modulation factor calculating unit is outside a predetermined range, and restarting the driving of the PWM type electromagnet driving unit 54 upon confirmation of satisfaction of predetermined conditions after the transfer to the hydrodynamic bearing mode to hereby return to the magnetic bearing mode.

More specifically, as shown in FIG. 1, the control mechanism 6 includes the PWM type electromagnet driving unit 54, the carrier component measuring unit 52 for measuring the carrier components of the voltage and current in the PWM type electromagnet driving unit 54, the rotating body position data and modulation factor calculating units 59, and a main control unit 50. The carrier component measuring unit 52 includes a voltage resonant circuit 55, a voltage wave detection circuit 56, a current resonant circuit 57, and a current wave detection circuit 58. In addition, the PWM type electromagnet driving unit 54 has a power amplifier.

Further, the control mechanism 6 in this embodiment has a motor control unit 53 for controlling the motor 34 in the impeller rotational torque generating unit (rotating body rotational torque generating unit) 3, and a motor current monitoring unit (rotating body rotational torque generating unit current monitoring unit) 51. Operations performed by the motor current monitoring unit may be carried out by the main control unit 50.

In this control mechanism 6, position control of the rotating body is carried out by use of the rotating body position data calculated by the rotating body position data and modulation factor calculating units 59. In addition, the bearing mode is changed by use of the modulation factor of carrier components which is calculated by the rotating body position data and modulation factor calculating units 59.

The rotating body position control carried out by use of the rotating body position data calculated by the rotating body position data and modulation factor calculating units 59 in the control mechanism 6 utilizes the theory described in the above-mentioned Non-Patent Document 1 which is referenced (and incorporated) here.

Figure 23:
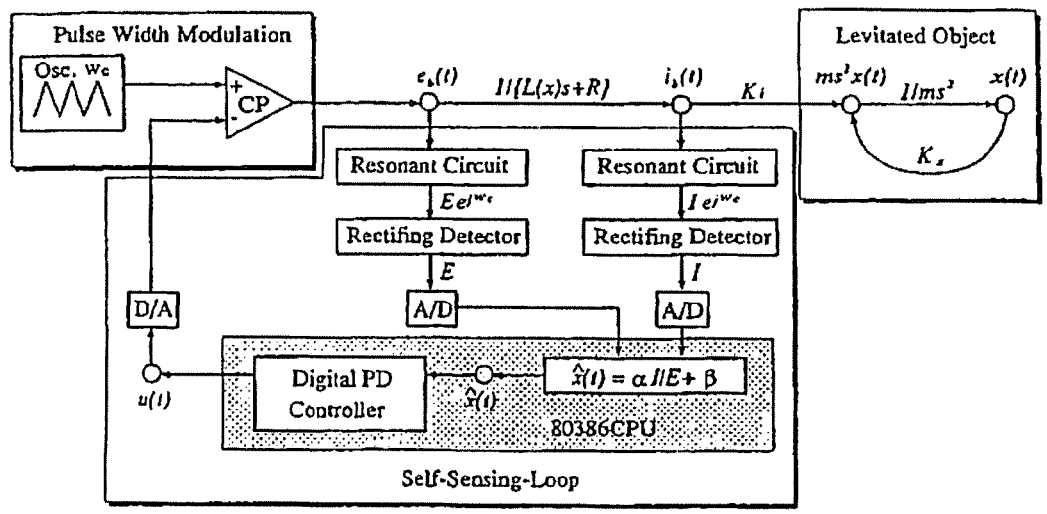
FIG. 23 is an outline of a sensorless type magnetic levitation system shown in Non-Patent Document 1.

FIG. 23 shows an outline of a sensorless type magnetic levitation system shown in Non-Patent Document 1. The equation of motion of a system having a single degree of freedom in the vertical direction is:

$$m(d^2/dt^2)x = mg - f(t) \quad (1)$$

(where $d^2/dt^2$ is the second-order differential with respect to time t)

$$f(t) = \mu_0 A N^2 i b^2 \quad (2)$$

$$= \mu_0 A N^2 (I_0 + \Delta ib)^2 / (X_0 + \Delta x)^2, \quad (3)$$

where
x: distance between levitated object and electromagnet
t: time
m: mass of levitated object
g: gravitational acceleration
f(t): magnetic attractive force generated by electromagnet
$\mu_0$: magnetic permeability in vacuum
A: sectional area of pole of electromagnet
N: number of turns of coil of electromagnet
ib: electromagnet current
$\Delta x$, $\Delta ib$: infinitesimal variations of x, ib
$X_0$, $I_0$: values of x, ib at balancing point, namely, levitation position.

Upon linearization on the assumption of minute vibrations in the vicinity of the balancing point, namely, the levitation position, the equation (1) is simplified as follows.

$$m(d_2/dt^2)\Delta x = (2mg/X_0)\Delta x + (-2mg/I_0)\Delta ib \quad (4)$$

The equation (4) indicates that it is necessary, for control of magnetic levitation, to know the distance x. The value of x can be obtained from data on the electromagnet without a position sensor, by use of the following equation:

$$X = \mu_0 A N^2 \omega_c I/E \quad (5)$$

where
E: amplitude of carrier component of voltage eb(t) of pulse width modulated rectangular wave signal for driving the electromagnet
I: amplitude of carrier component of electromagnet current ib(t)
$\omega_c$: angular frequency of pulse width modulated rectangular wave signal for driving the electromagnet.

Therefore, $$eb(t) = E\exp(j\omega_c t) \quad (6a)$$

$$ib(t) = I\exp(j\omega_c t) \quad (6b).$$

The equation (5) indicates that it is necessary to obtain I/E, for obtaining the distance x.

Here, I/E is expressed as follows:

$$I/E = (I_H - I_L)/[4Eb\pi(p - p^2)] \quad (7),$$

where
$I_H$: initial condition of ON time of current in the case where electromagnet is driven by pulse width modulated rectangular wave signal
$I_L$: initial condition of OFF time of current in the case where electromagnet is driven by pulse width modulated rectangular wave signal
Eb: amplitude of voltage eb(t) of pulse width modulated rectangular wave signal for driving the electromagnet
p: modulation factor of voltage eb(t) of pulse width modulated rectangular signal for driving the electromagnet; also called "duty ratio".

Therefore, $$eb(t) = \begin{cases} +Eb & (0 < t < pT) & (8a) \\ -Eb & (pT < t < T) & (8b) \end{cases}$$

(T: period of eb(t))

From the equation (5) and the equation (7), it is seen that, for obtaining the distance x from the data on the electromagnet, it is necessary to measure I and E and to take into account the influence of the modulation factor p.

Figure 24:
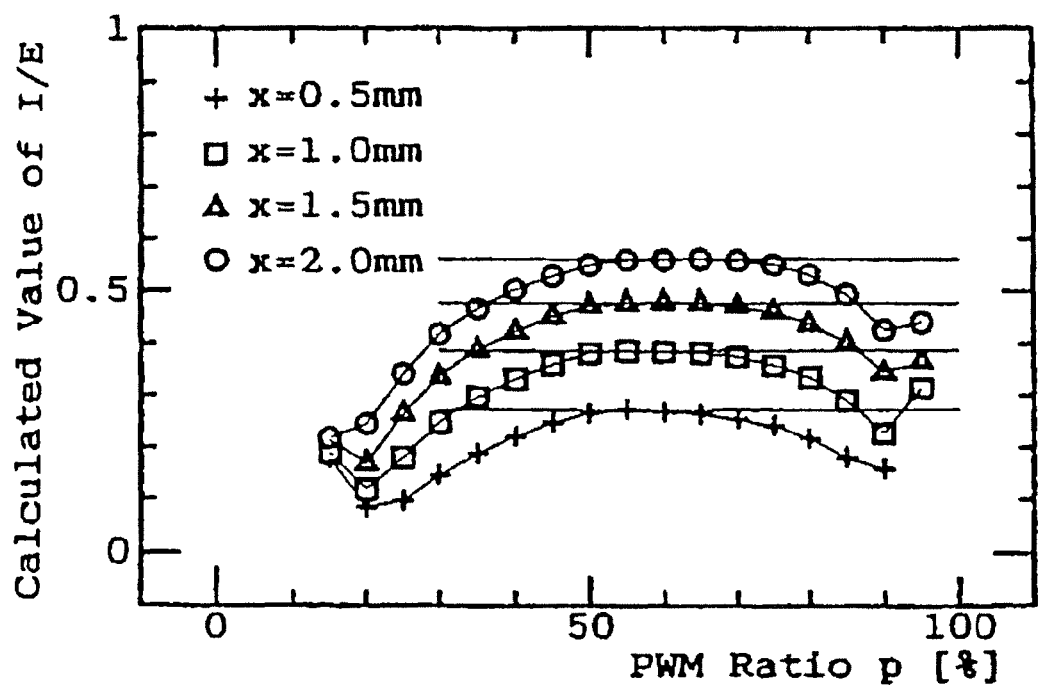
FIG. 24 is a diagram showing experimental results for the sensorless type magnetic levitation system shown in Non-Patent Document 1.

In Non-Patent Document 1, the results shown in FIGS. 24 and 25 here are obtained from experiments. FIG. 24 shows that the output characteristic I/E is not constant but varies with the modulation factor p, even when the distance x is kept constant. It is also shown, however, that the practical driving is conducted with p=50% or more, and a substantially constant output characteristic is obtained over a modulation factor range from 50 to 80%, so that levitation control by self-sensing using the electromagnet (position sensing by the electromagnet without using a position sensor) can be achieved in this modulation factor range.

Therefore, when the modulation range is in a predetermined range, the rotating body position data can be obtained from the measured I and E values, without any special consideration of the modulation factor.

In the blood pump apparatus disclosed here, a rotating body position control is conducted by a method in which rotating body position data is calculated by use of carrier data according to the above-mentioned control theory, and the PWM type electromagnet driving unit 54 is controlled by utilizing the rotating body position data thus obtained.

Specifically, based on the position data on the rotating body, when the distance between the rotating body and the electromagnet is relatively large, the pulse width is enlarged (the modulation factor p is enhanced). On the contrary, when the distance between the rotating body and the electromagnet is relatively small, the pulse width is reduced (the modulation factor p is lowered). It is to be noted here, however, that a magnetic levitation system is usually an unstable system and so it is thus necessary to stabilize the system by applying a feedback control to the electromagnet driving current. As a method of stabilizing through a feedback control, there may be used PD control or PID control.

Furthermore, it has been reported that when digital PD compensation of an estimated displacement in the vicinity of the balancing point was conducted based on the characteristic shown in FIG. 24 to thereby perform a levitation control, a stable levitation characteristic was obtained, though a minute vibration was left steadily.

The magnetic levitation technology without a position sensor thus has a problem in that, although magnetic levitation is possible in the vicinity of a balancing point, the conditions under which position control is possible are limited by the modulation factor p. The limitation by the modulation factor p means that, in the case where the controlled system comes off far from the balancing point due to a large disturbance such as a shock, the control system brings the attracting force of the electromagnet to a very low value or a very high value so as to return the controlled system to the balancing point, and the modulation factor p therefore takes a value approximate to 0 or 1, which makes the position control impossible. In other words, the range in which the position control is possible is limited.

Accordingly, it is difficult to directly apply the technology of Non-Patent Document 1 to a blood pump for an artificial heart, because of the problem that upon a large disturbance such as a shock, the rotating body and the housing come into contact with each other during rotation, possibly exerting a bad influence on the patient.

In view of this, the control mechanism associated with the blood pump apparatus here is so configured that, to address the generation of a disturbance, the modulation factor of the voltage of a pulse width modulated rectangular wave signal for driving the electromagnet is calculated, and a change-over of the bearing mode is determined by utilizing the modulation factor thus calculated. As the modulation factor in this control, the modulation factor of the current of the pulse width modulated rectangular wave signal for driving the electromagnet may be calculated.

The modulation factor is calculated as follows. The modulation factor p is the ratio of the period during which the pulse width modulated signal is ON (t=0 to pT) to the period T (=2π/ωc) of the carrier wave, and it can therefore be obtained by counting the clock pulses within the ON period by use of a clock for counting, for example. The modulation factor p can also be obtained by use of an A-D converter.

More specifically, in the pump apparatus shown in FIG. 1, the electromagnet is driven with pulse width modulation. As for the driving voltage and the driving current, individual PWM carrier components E and I thereof are extracted by the above-mentioned resonant circuits and wave detection circuits. From the E and I thus obtained and the modulation factor (duty ratio) p of the PWM waveform at that time, digital PD compensation (or PID compensation) of an estimated distance is conducted based on preliminarily stored data (Table or the following calculation formula (9)) and a digital controller, and a control command value necessary for magnetic levitation is sent to the control unit.

$$z=a(I/E)+b \quad (9)$$

(a and b are preliminarily obtained constants)

The above-mentioned equation (5) is an equation for the case where the condition of $\mu_s \gg L$ is established between the relative permeability $\mu_s$ of a magnetic member and the length L of the magnetic member. In the case where $L/\mu_s$ is not negligible with reference to x, $$x=\mu_0 AN^2 \omega_c (I/E)-(L/\mu_s).$$

Here, by substitution:

$$a=\mu_0 AN^2 \omega_c, \text{ and}$$

$$b=-L/\mu_s,$$

the equation (9) is obtained.

Therefore, z in the equation (9) is the calculated value of x obtained from I and E. The equation (9) corresponds to Equation (12) in Non-Patent Document 1. In FIG. 1 of Non-Patent Document 1 (FIG. 23 in the present application), the equation (9) is $$\hat{x}(t)= \ldots$$

but z is used here, for easy description.

Then, based on the modulation factor p of the PWM waveform and the motor current (in this embodiment), it is determined whether the magnetic bearing is to be adopted or the hydrodynamic bearing is to be adopted. In the latter case, the driving of the electromagnet is stopped.

The control mechanism 6 in this embodiment stores a predetermined modulation factor range, and the bearing mode changing-over means functions to stop the driving of the PWM type electromagnet driving unit 54 so as to make a shift to the hydrodynamic bearing mode when the modulation factor calculated by the modulation factor calculating unit is outside the predetermined modulation factor range.

The bearing mode change-over system in the control mechanism 6 will be described, referring to the embodiment shown in FIGS. 1 and 9.

Figure 9:
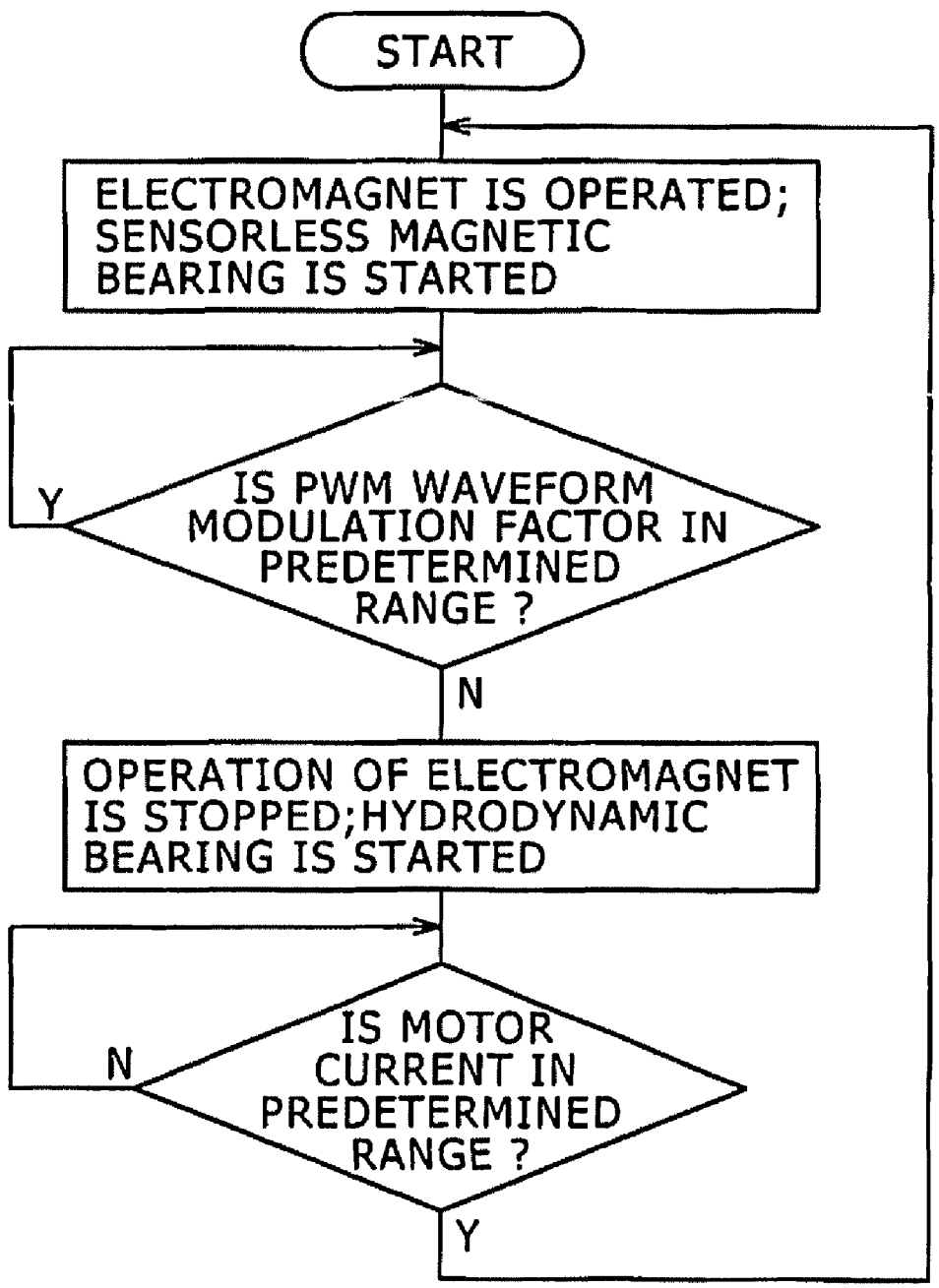
FIG. 9 is a flowchart illustrating the operation of the sensorless magnetic bearing type blood pump apparatus according to one disclosed embodiment.

The control mechanism 6 for carrying out the embodiment shown in FIG. 9 stores a predetermined modulation factor range. Specifically, the predetermined modulation factor range (for example, 50%≦p≦80%) is stored in the main control unit 50.

As shown in FIG. 9, when the operation of the blood pump apparatus 10 is started, the PWM type electromagnet driving unit 54 is operated, to operate the electromagnet 41. In addition, the motor control unit is also operated to rotate the rotating body in a magnetically levitated condition (magnetic bearing condition).

Then, it is determined whether or not the modulation factor calculated serially is in the predetermined modulation factor range stored as above. When the calculated modulation factor is in the range, the magnetic bearing condition is continued. As shown in FIG. 9, when the calculated modulation factor is determined to be outside the predetermined range stored, the operation of the PWM type electromagnet driving unit is stopped, and the operation of the electromagnet 41 is thereby stopped. As a result, though the rotating body comes close to the rotating body rotational driving unit side (the motor side), the rotation of the rotating body by the motor is continued so that transition (change-over) to the hydrodynamic bearing condition or mode by the hydrodynamic grooves is effected, and the rotating body is rotated in the hydrodynamic bearing condition or mode.

In addition, the control mechanism in this embodiment has a motor current monitoring mechanism as above-mentioned. Specifically, the serial motor current is detected by a motor current monitoring unit, and the detection data is sent to the main control unit 50. The main control unit 50 stores a predetermined rotating body rotational torque generating unit current range (specifically, a predetermined motor current range). When a rotating body rotational torque generating unit current in the predetermined rotating body rotational torque generating unit current range stored is detected by a rotating body rotational torque generating unit current monitoring function after the transition (change-over) to the hydrodynamic bearing mode, it is determined that the predetermined conditions are fulfilled. In this case, as shown in FIG. 9, the PWM type electromagnet driving unit 54 is driven to rotate the electromagnet 41, whereby return to the magnetic bearing mode is realized. It is considered that the predetermined rotating body rotational torque generating unit current is set in a range near the rotating body rotational torque generating unit current at the time of normal rotation with the magnetic bearing.

Figure 10:
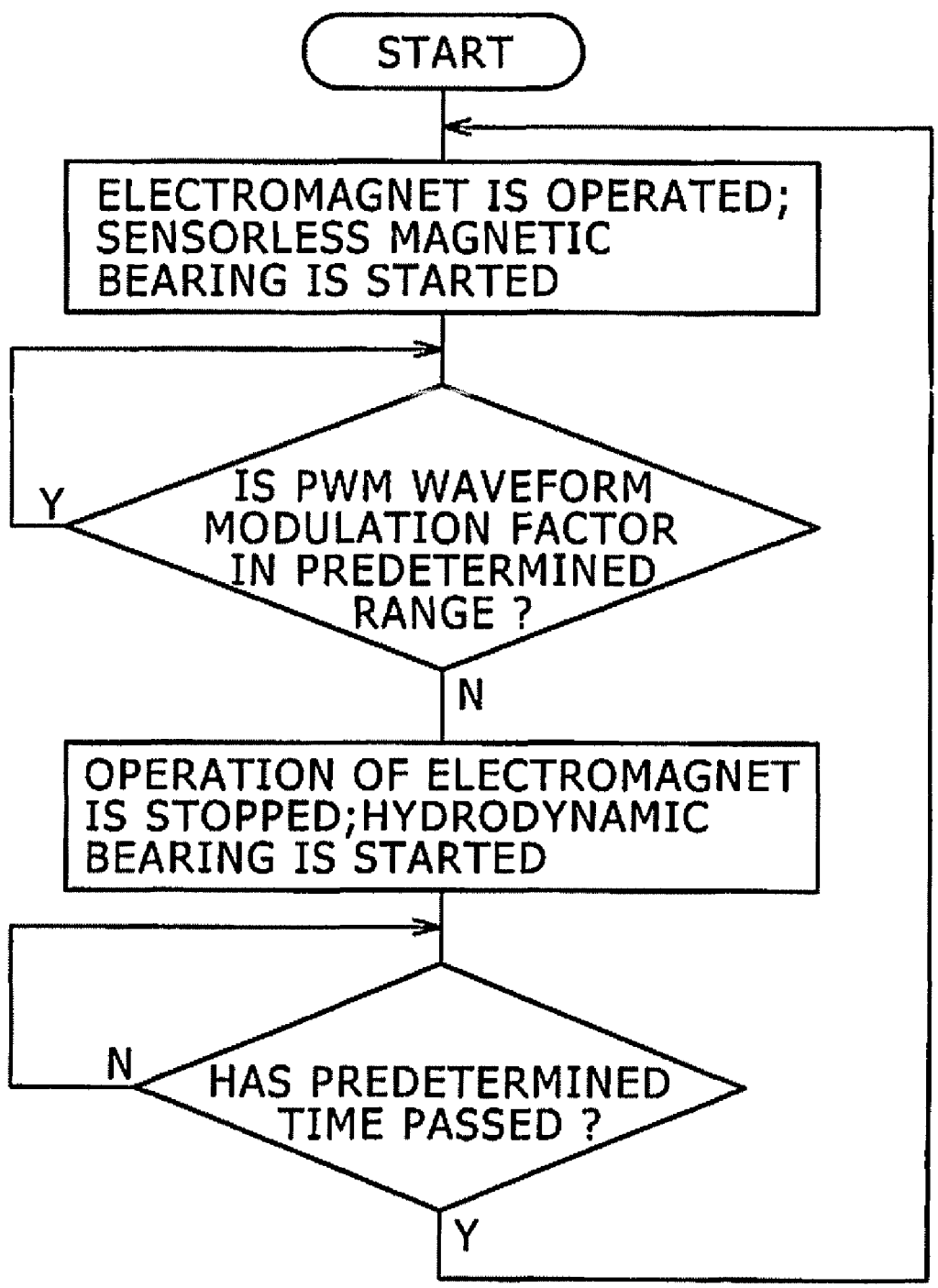
FIG. 10 is a flowchart illustrating the operation of a sensorless magnetic bearing type blood pump apparatus according to another disclosed embodiment.

The bearing mode change-over system or means in the control mechanism 6 is preferably the one described above, but may also be one according to the embodiment shown in FIG. 10. The bearing mode change-over system or means in this embodiment differs from the above-described bearing mode change-over system or means only with respect to the predetermined conditions which are satisfied for return to the magnetic bearing mode.

In the bearing mode change-over system or means in this embodiment, also, during rotation of the rotating body in the magnetically levitated condition (magnetic bearing condition), it is determined whether or not the modulation factor calculated serially is within the stored predetermined modulation factor range. When the calculated modulation factor is within the stored range, the magnetic bearing condition is continued. As shown in FIG. 10, when the calculated modulation factor is determined to be outside the stored predetermined modulation factor range, the operation of the PWM type electromagnet driving unit is stopped, and the operation of the electromagnet 41 is thereby stopped. As a result, although the rotating body comes close to the rotating body rotational driving unit side (the motor side), transition (change-over) to the hydrodynamic bearing mode or condition by the hydrodynamic grooves is effected, and the rotating body is rotated in the hydrodynamic bearing condition or mode.

In addition, the bearing mode change-over system or means in the control mechanism in this embodiment has a timer function in which a timer is operated immediately upon transition (change-over) to the hydrodynamic bearing mode. When the lapse of a predetermined time (for example, 0.5 to 5 min) is detected after such change-over, it is determined that the predetermined conditions are fulfilled. In this instance, as shown in FIG. 10, the PWM type electromagnet driving unit 54 is driven, to operate the electromagnet 41, whereby return to the magnetic bearing mode is effected.

In the sensorless magnetic bearing type blood pump apparatus disclosed here, when the conditions for permitting the operation of the sensorless magnetic bearing come to be unsatisfied due to some cause, transition (change-over) to the hydrodynamic bearing mode is immediately made. When the conditions for permitting the operation of the sensorless magnetic bearing are again satisfied due, for example, to the return of the rotating body to a position where it can be rotated with the sensorless magnetic bearing, return to the sensorless magnetic bearing mode is immediately made.

Since the need for a position sensor is eliminated, it is possible to realize reductions in size, power consumption, and price of the apparatus, on the basis of the whole system including the pump and the controller. In addition, since the need for a cable for connection between a position sensor in the pump and an extracorporeal controller is eliminated, the cable can be made smaller in diameter, and the risk of infection can be lowered.

The apparatus disclosed in the above-mentioned Patent Document 2 is one in which an electromagnet is used auxiliary, and is not one in which the position of a rotating body is estimated accurately. In the sensorless magnetic bearing type blood pump apparatus disclosed in the present application, the position of the rotating body can be estimated at a certain level, based on the above-mentioned theory. It is possible to achieve magnetic bearing with a certain distance between the rotating body and the housing so that the apparatus is quite good from the viewpoint of preventing the generation of hemolysis or thrombus.

The shape of the blood pump used in the sensorless magnetic bearing type blood pump apparatus in the present invention is not limited to the above-mentioned.

Figure 11:
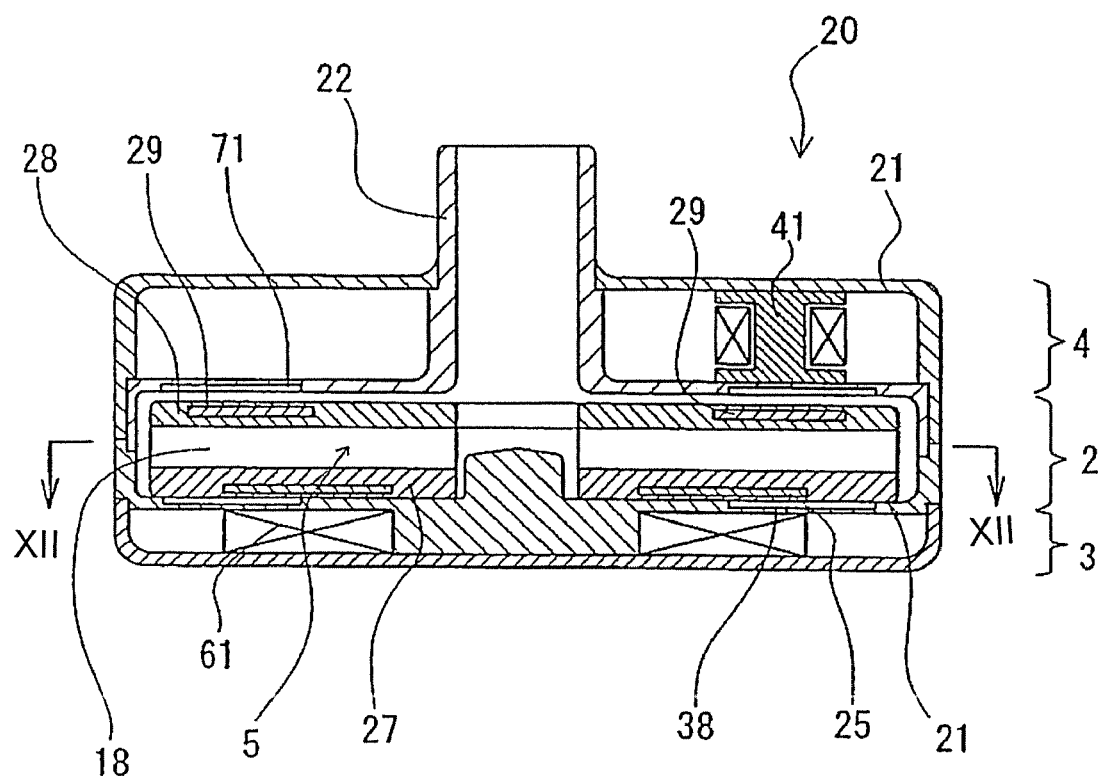
FIG. 11 is a longitudinal cross-sectional view of an example of the blood pump used in a sensorless magnetic bearing type blood pump apparatus according to another disclosed embodiment.
Figure 12:
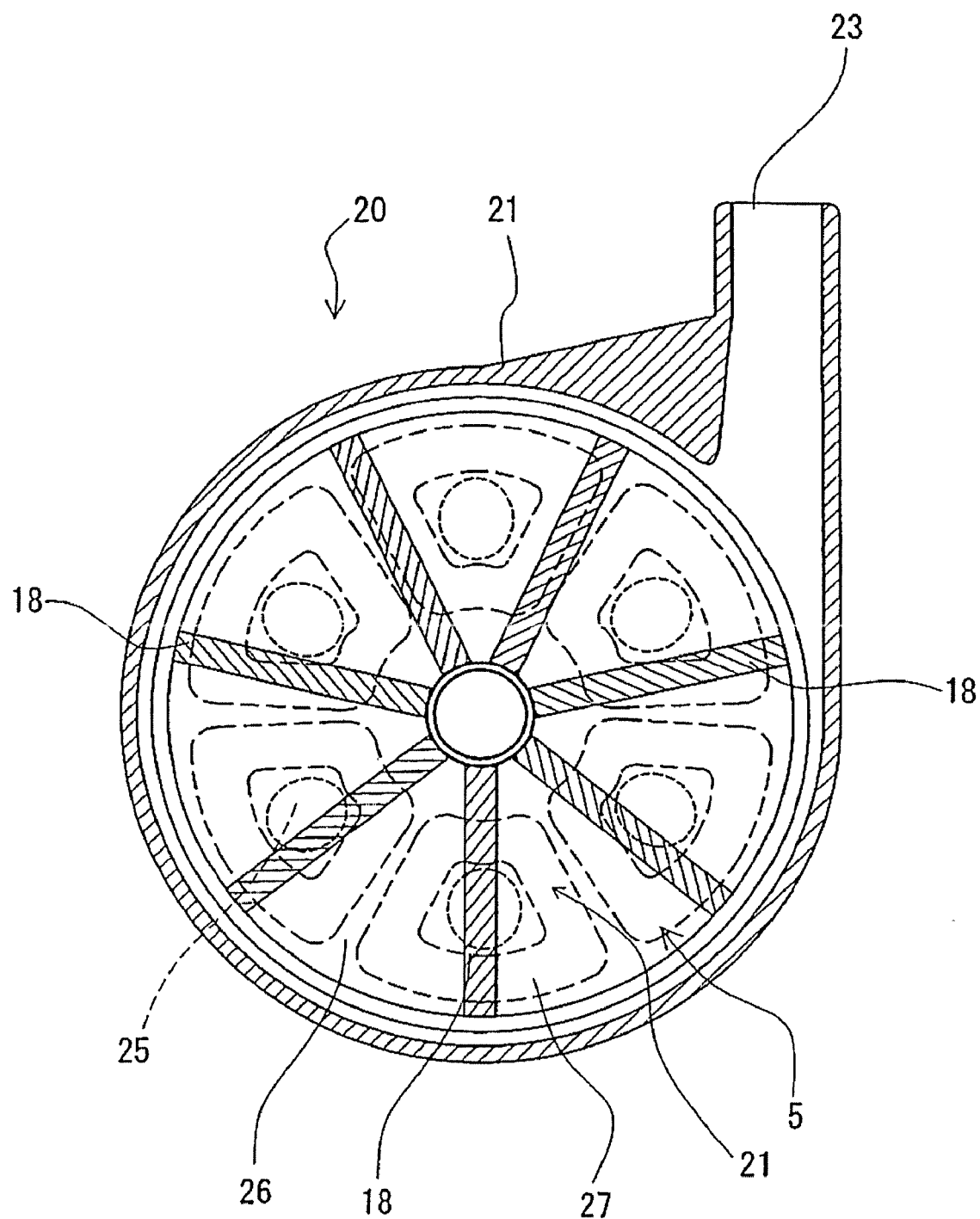
FIG. 12 is a cross-sectional view of the blood pump shown in FIG. 11 taken along the section line XII-XII in FIG. 11.

For example a blood pump of the type shown in FIGS. 11 and 12 may also be used. This blood pump 20 differs from the above-described blood pump 10 only in the configuration of the impeller rotational torque generating unit 3.

The blood pump 20 in this embodiment has a configuration in which, as shown in FIGS. 11 and 12, the impeller rotational torque generating unit 3 comprises a stator coil motor having a plurality of stator coils 61 arranged in a circular pattern for attracting magnetic bodies 25 of the impeller 5 from one side of the impeller 5 and rotating the magnetic bodies 25 when energized.

The stator coils 61 are plural in number and are arranged on the circumference of a circle at substantially equal angular intervals about the center of the circle. In the illustrated embodiment, six stator coils are provided. As the stator coils, stator coils of the multilayer winding type are used in the illustrated embodiment. By changing over the direction of the current flowing in each of the stator coils 61, a rotating magnetic field is generated, and the rotating body is attracted and rotated by the rotating magnetic field.

As shown in FIG. 12, a plurality of magnetic bodies 25 (permanent magnets, driven magnets) are embedded in the impeller 5. As an example, six to twelve magnetic bodies 25 can be provided. In this embodiment, the magnetic bodies 25 are embedded in a lower shroud 27. The magnetic bodies 25 embedded in the rotating body are attracted in a direction opposite a blood inflow port 22 by the stator coils 61 of the impeller rotational torque generating unit 3, are coupled with the operation of the stator coils 61, and transmit a rotational torque to the rotating body.

In addition, by embedding a certain number of magnetic bodies 25 as in this embodiment, the magnetic coupling of the magnetic bodies 25 with the stator coils 61 as will be described later can be secured sufficiently. Preferably, the magnetic bodies 25 are each substantially trapezoidal in shape. The magnetic bodies 25 may each be ring-like or plate-like. The number and layout pattern of the magnetic bodies 25 preferably correspond to the number and layout pattern of the stator coils 61. Preferably, the plurality of magnetic bodies 25 are arranged on the circumference of a circle so that their magnetic poles are alternately different and are arranged so that they are at substantially equal angular intervals about the center axis of the rotating body.

The magnetic bearing type blood pump used in the sensorless magnetic bearing type blood pump apparatus according to the present invention may be either a centrifugal blood pump or an axial flow blood pump. Furthermore, the form of the magnetic bearing may be either an "axial gap" type (the type involving controlling a gap in the same direction as the rotation axis of the pump) or a "radial gap" type (the type involving controlling a gap in a direction orthogonal to the rotation axis of the pump). There are the following four types of blood pumps.

1) Axial Gap Type Centrifugal Blood Pump

The above-mentioned blood pumps 10 and 20 are this type of blood pump.

2) Radial Gap Type Centrifugal Blood Pump

A blood pump 100, described later, is this type of blood pump.

3) Axial Gap Type Axial Flow Blood Pump

A blood pump 200, described later, is this type of blood pump.

4) Radial Gap Type Axial Flow Blood Pump

A blood pump 300, described later, is this type of blood pump.

Details and aspects of the blood pump 100 shown in FIGS. 13-16 will be described. The blood pump 100 is a radial gap type centrifugal blood pump.

The blood pump 100 includes: a housing 121 having a liquid inflow port 122 and a liquid outflow port 123; a blood pump unit having a rotating body 105 rotated in the housing 121 and feeding a liquid by centrifugal force at the time of rotation; a rotating body rotational torque generating unit (impeller rotational torque generating unit, specifically stator coils) that includes a stator motor 161 for attracting first magnetic bodies 125 disposed in the inside of a rotor 106 provided beneath the rotating body 105 and rotating the rotor 106; and hydrodynamic grooves 138 provided in a side surface of the rotor 106 and constituting a hydrodynamic bearing section. The blood pump apparatus 100 has electromagnets 141 for attracting the first magnetic bodies 125 or second magnetic bodies 129, provided separately from the first magnetic bodies 125, of the rotor 106 in a direction (radial direction) orthogonal to the direction of the axis of rotation by the rotating body rotational torque generating unit (stator coils) and for levitating the rotating body 105 (together with the rotor 106).

Figure 13:
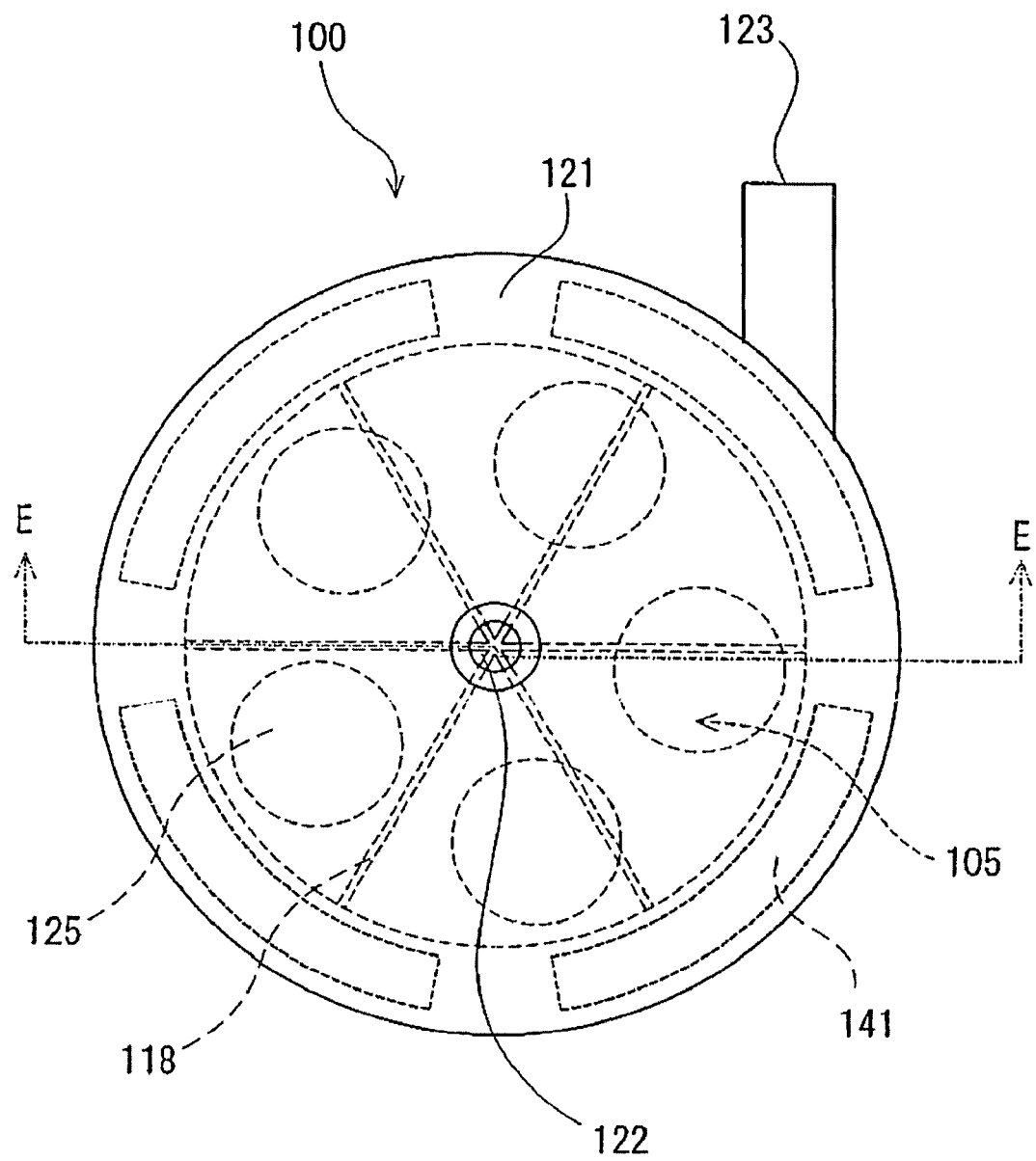
FIG. 13 is a plan view of an example of the blood pump used in a sensorless magnetic bearing type blood pump apparatus according to another disclosed embodiment.

As shown in FIG. 13, in this blood pump 100, two electromagnets are disposed opposite to each other with the rotating body (rotor) therebetween in the X direction which is a horizontal direction relative to the bottom surface of the rotating body (rotor), and two electromagnets are disposed opposite to each other with the rotating body (rotor) therebetween in the Y direction which is a horizontal direction and orthogonal to the X direction. With this configuration, a magnetic bearing for controlling a gap in the radial direction is formed. The four electromagnets are each comprised of a core and a coil wound around the core.

Permanent magnets 129 are embedded in the rotor 106 beneath the rotating body 105 as mentioned above, and sufficient attractive forces are generated between the permanent magnets 129 and the four electromagnets 141. In addition, as mentioned above, a plurality of magnetic bodies 125 are embedded in the inside of the rotor 106. The magnetic bodies 125 are preferably permanent magnets. The layout form of the magnetic bodies 125 and the stator motor 161 may preferably be the same as described above in connection with the blood pump 20.

As shown in FIG. 15, a side surface 106a of the rotor 106 is provided with hydrodynamic grooves 138 forming a hydrodynamic bearing section. Particularly, the hydrodynamic grooves 138 in this embodiment are grooves positioned in a herringbone pattern. The hydrodynamic grooves 138 are plural in number and are inclined at a predetermined angle relative to the center axis of the rotor and are arranged in a ring form while being parallel to each other and spaced at equal or regular intervals. As illustrated in FIG. 15, the hydrodynamic grooves 138 are arranged in two rows so that the grooves in the two rows are symmetrical with each other with respect to the center line between the two rows. This helps ensure that the hydrodynamic grooves 138 are arranged in the so-called herringbone pattern.

Furthermore, as shown in FIG. 16, the bottom surface 106b of the rotor 106 is provided with a plurality of second hydrodynamic grooves 173. The second hydrodynamic grooves 173 may be formed in the inside surface of the housing, facing the bottom surface of the rotor 106. The second hydrodynamic grooves 173 may be the grooves that are the same as the hydrodynamic grooves 73 described above with reference to the blood pump 10.

In this blood pump 100, at the time of rotation with the hydrodynamic bearing, no current flows in the four electromagnets 141 provided at side surface on the outside of a blood chamber. However, since the second magnetic bodies (permanent magnets) embedded in the rotor 106 and the cores in the electromagnets 141 attract each other, the rotor 106 is moved little in the direction of the rotation axis of the rotating body (the axial direction), but in the radial direction, it is attracted by the stator motor and therefore tends to adhere to some portion of the inside surface of the housing. If the rotation of the rotor can be maintained, when the rotor comes into proximity to the side surface of the housing, the dynamic grooves provided in the side surface of the rotor in the proximity area generate a pressure, and a force for spacing the rotor away from the housing arises from the pressure so that non-contact rotation is maintained. In addition, the hydrodynamic grooves provided in the lower surface of the rotor 106 help ensure that when the rotor tends to move toward the stator motor, a force in the opposite direction arises from the pressure generated by the hydrodynamic grooves in the lower surface of the rotor so that non-contact rotation is maintained.

Figure 17:
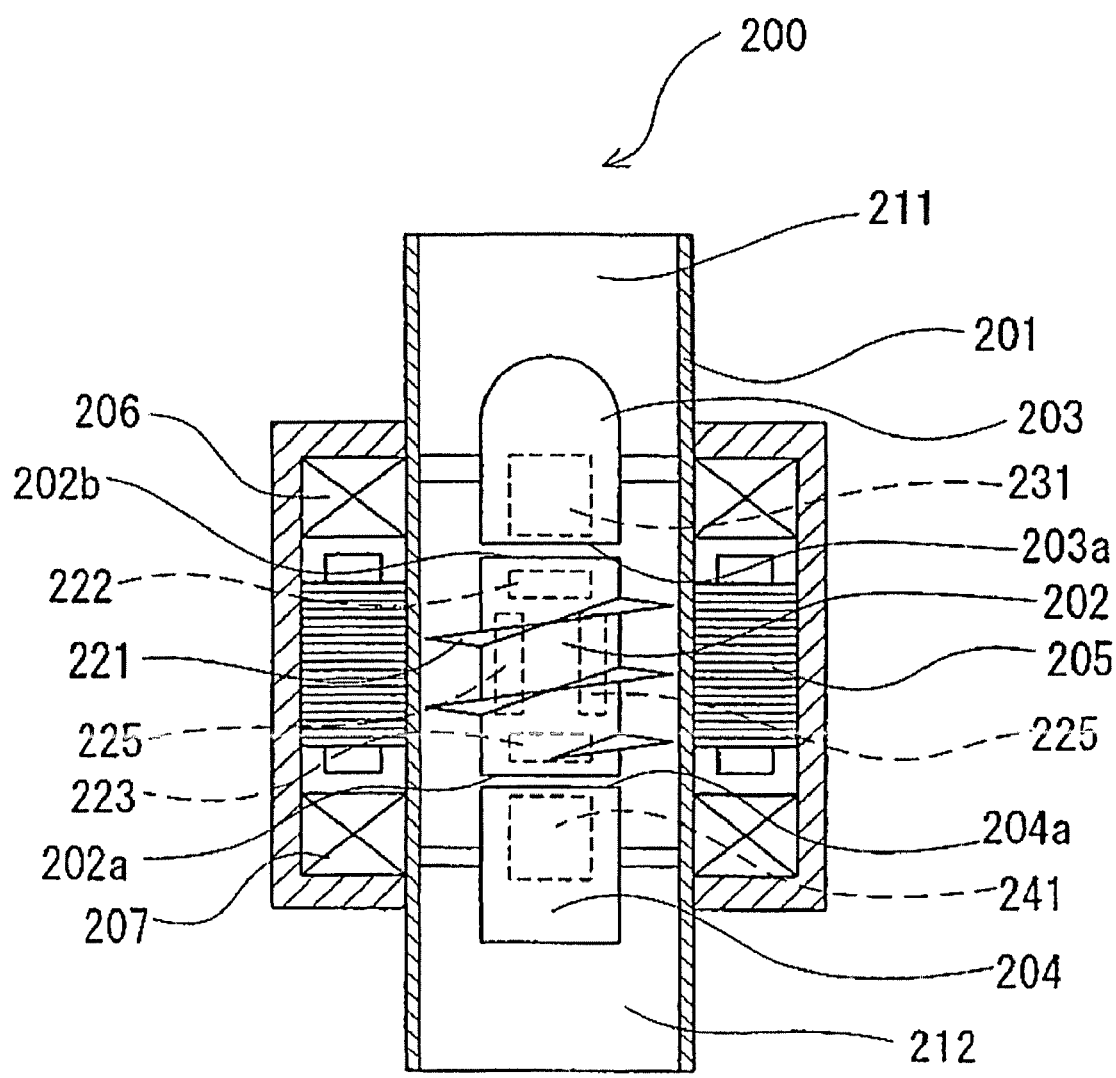
FIG. 17 is a longitudinal cross-sectional view of an embodiment of the blood pump used in a sensorless magnetic bearing type blood pump apparatus according to another disclosed embodiment.
Figure 18:
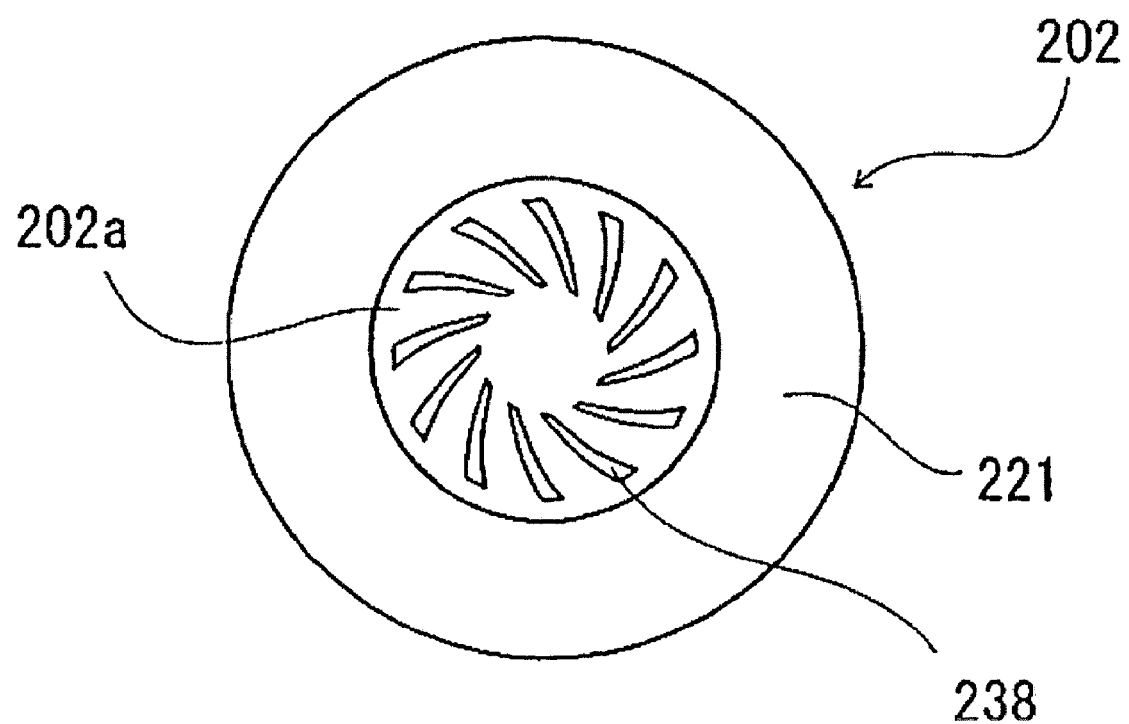
FIG. 18 is a bottom view of a rotating body used in the blood pump shown in FIG. 17.
Figure 19:
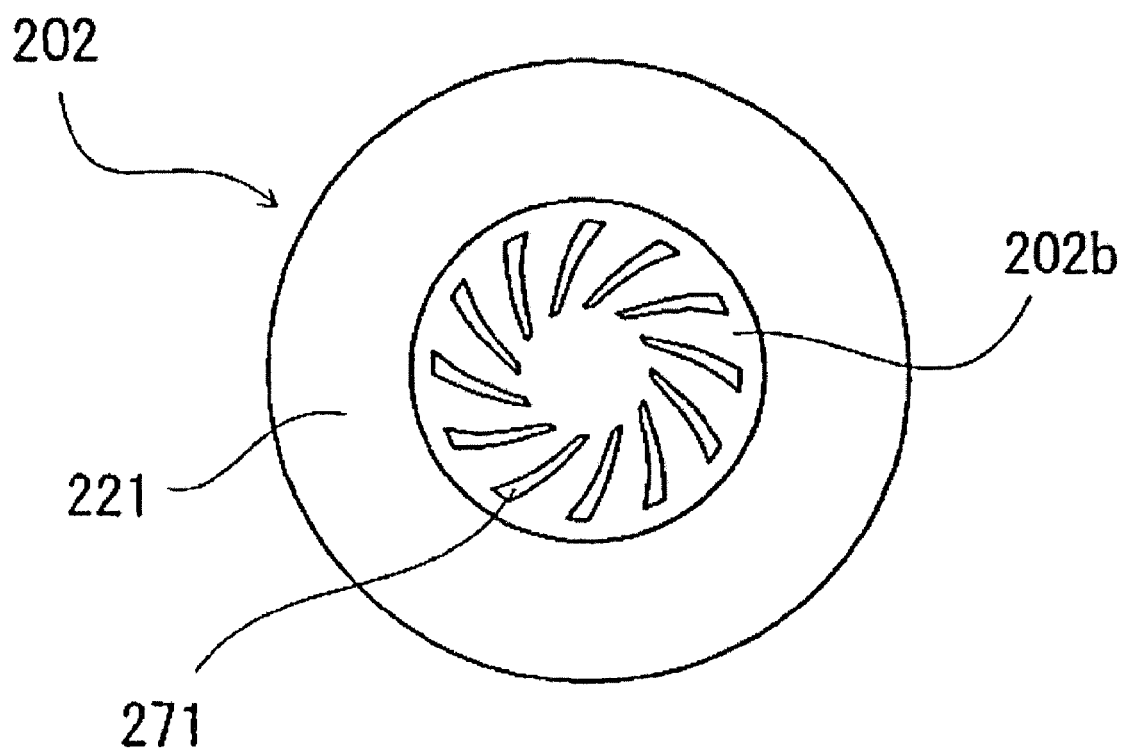
FIG. 19 is a plan view of the rotating body used in the blood pump shown in FIG. 17.

A blood pump 200 in the form of an axial gap type axial flow pump is shown in FIGS. 17-19. The blood pump 200 in this embodiment also includes: a housing 201 having a blood inflow port 211 and a blood outflow port 212; a rotating body 202 provided with magnetic bodies 225 and rotated in the housing 201 in a non-contact condition relative to the inside surface of the housing 201 to feed blood; a rotating body rotational torque generating unit 205 for rotating the rotating body 202 by acting thereon from the outside of the housing 201; magnetic bearing units 206, 207 for permitting the rotating body 202 to be rotated in a non-contact condition in the housing 201; and a hydrodynamic bearing section for permitting the rotating body 202 to be rotated in a non-contact condition in the housing 201 when the operation of the magnetic bearing units 206, 207 is stopped.

In this blood pump 200, the housing 201 is formed in a hollow cylindrical shape as shown in FIG. 17, and is provided with a blood inflow port 211 on its upper end side and a blood outflow port 212 on its lower end side.

A cylindrical rotating body 202 is contained in the housing 201. A blood conveying fin 221 is provided on the side surface of the rotating body 202. The rotating body 202 is also provided therein with side surface side magnetic bodies 225 to be supplied with a rotating force from a rotating body rotational torque generating unit, an upstream-side magnetic body 222 provided in the inside of and on the upper end side of the rotating body 202, and a downstream-side magnetic body 223 provided in the inside of and on the lower end side of the rotating body 202. The side surface side magnetic bodies 225, the upstream-side magnetic body 222 and the downstream-side magnetic body 223 are each composed of a magnetic material or a permanent magnet, preferably permanent magnets.

In addition, the housing 201 has an upstream-side rotating body attracting section 203, disposed in the vicinity of and on the upstream side of the rotating body 202 and provided therein with a magnetic member 231. Specifically, the upstream-side rotating body attracting section 203 is a part called a "straightener", and its upper end is formed in a substantially hemispherical shape as shown for permitting good dispersion of blood. The magnetic member 231 provided in the upstream-side rotating body attracting section 203 and the upstream-side magnetic body 222 provided in the rotating body 202 attract each other magnetically.

The housing 201 also has a downstream-side rotating body attracting section 204 disposed in the vicinity of and on the downstream side of the rotating body 202 and provided therein with a magnetic member 241. Specifically, the downstream-side rotating body attracting section 204 is a part called a "diffuser". The magnetic member 241 provided in the downstream-side rotating body attracting section 204 and the downstream-side magnetic body 223 provided in the rotating body 202 attract each other magnetically. Therefore, the rotating body is in the state of being pulled in both directions toward the upper end and toward the lower end (upstream and downstream). The magnetic member 231 provided in the upstream-side rotating body attracting section 203 and the magnetic member 241 provided in the downstream-side rotating body attracting section 204 are each composed of a magnetic material or a permanent magnet.

In the blood pump 200 in this embodiment, the rotating body rotational torque generating unit includes a stator coil motor 205 having a plurality of stator coils which are so arranged as to surround the side surface of the rotating body 202 for attracting the magnetic bodies 225 of the rotating body 202 and rotating the rotating body 202 when energized.

Further, in the blood pump 200 in this embodiment, a non-contact bearing mechanism has magnetic bearing means, which includes a first coil body 206 for giving a magnetic force to or amplifying a magnetic force of the magnetic member 231 of the upstream-side rotating body attracting section 203 when energized, and a second coil body 207 for giving a magnetic force to or amplifying a magnetic force of the magnetic member 241 of the downstream-side rotating body attracting section 204 when energized. The first coil body 206 cooperates with the magnetic member 231 of the upstream-side rotating body attracting section 203 in constituting a first electromagnet. Similarly, the second coil body 207 cooperates with the magnetic member 241 of the downstream-side rotating body attracting section 204 in constituting a second electromagnet. The magnetic bearing mechanism in the blood pump 200 in this embodiment is composed of the two coil bodies 206, 207, the above-mentioned upstream-side magnetic body 222 and downstream-side magnetic body 223 of the rotating body 202, the magnetic member 231 of the upstream-side rotating body attracting section 203, and the magnetic member 241 of the downstream-side rotating body attracting section 204. By controlling the current supplied to the two coil bodies 206 and 207, the rotating body 202 is rotated without making contact with any portion of the housing inside surface inclusive of the upstream-side rotating body attracting section 203 and the downstream-side rotating body attracting section 204.

The pump apparatus including the blood pump in this embodiment has a control mechanism equivalent to that described in the above-described embodiment. The control mechanism includes: a PWM type electromagnet driving unit for driving the first coil body 206 constituting the first electromagnet and the second coil body 207 constituting the second electromagnet; a carrier component measuring unit for measuring the carrier components of the voltage and current in the PWM type electromagnet driving unit; rotating body position data and modulation factor calculating units for respectively calculating rotating body position data and the modulation factor of a pulse width modulated waveform by use of the carrier wave data measured by the carrier component measuring unit; a rotating body position controlling unit or means for controlling the PWM type electromagnet driving unit by utilizing the rotating body position data calculated by the rotating body position data calculating unit; and a bearing mode changing-over means for effecting transition (change-over) to the hydrodynamic bearing mode by stopping the driving of the PWM type electromagnet driving unit 54 when the modulation factor calculated by the modulation factor calculating unit is outside a predetermined range and for restarting the driving of the PWM type electromagnet driving unit so as to return to the magnetic bearing mode upon confirming satisfaction of predetermined conditions after the transition (change-over) to the hydrodynamic bearing mode.

In addition, as shown in FIG. 18, the rotating body 202 has hydrodynamic grooves 238 formed in its surface (bottom surface) 202 facing the downstream-side rotating body attracting section (diffuser) 204. The hydrodynamic grooves 238 constitute a hydrodynamic bearing section. The hydrodynamic grooves 238 may alternatively be formed in a surface of the downstream-side rotating body attracting section (diffuser) 204 facing the bottom surface of the rotating body 202. As the hydrodynamic grooves 238, grooves that are the same as the hydrodynamic grooves 38 described in relation to the blood pump 10 above can be used.

The hydrodynamic bearing section is not limited to the above-mentioned hydrodynamic grooves 238, but may include a deformed surface (specially shaped surface) provided at the surface (bottom surface) 202a of the rotating body 202 facing the downstream-side rotating body attracting section (diffuser) 204, or at the surface 204a of the downstream-side rotating body attracting section (diffuser) 204 facing the bottom surface 202a of the rotating body 202.

Furthermore, as shown in FIG. 19, in the blood pump 200 in this embodiment, the rotating body 202 has second hydrodynamic grooves 271 formed in its surface (top surface) 202b facing the upstream-side rotating body attracting section (straightener) 203. The second hydrodynamic grooves 271 may alternatively be provided in the surface of the upstream-side rotating body attracting section (straightener) 203 facing the top surface of the rotating body 202. As the hydrodynamic grooves, grooves that are the same as the hydrodynamic grooves 38 or hydrodynamic grooves 71 described in relation to the blood pump 10 above can be used.

In addition, the second hydrodynamic bearing section may include a deformed surface (specially shaped surface) provided at the surface (top surface) 202b of the rotating body 202 facing the upstream-side rotating body attracting section (straightener) 203, or at the surface 203a of the upstream-side rotating body attracting section (straightener) 203 facing the top surface of the rotating body 202.

In this blood pump 200, at the time of rotation in a hydrodynamic bearing mode, no current flows in the two coil bodies 206, 207 provided on the outside of a blood chamber. However, since the permanent magnets 222, 223 embedded in the rotating body 202 and the magnetic members 231, 241 incorporated in the straightener 203 and the diffuser 204 attract each other in opposite directions, the rotating body is little moved in the radial directions (the directions orthogonal to the direction of the axis of rotation), and tends to adhere either to the straightener 203 and the diffuser 204 located in the axial direction relative to the rotating body. Since the position of the rotating body in the radial directions is little changed, the motor functions properly, and the rotating body is rotated. If the rotation is maintained, the pressures generated by the hydrodynamic grooves provided in the top surface and the bottom surface of the rotating body prevent the rotating body from adhering to the straightener 203 or the diffuser 204 so that the rotating body is kept rotating in a non-contact condition.

Figure 20:
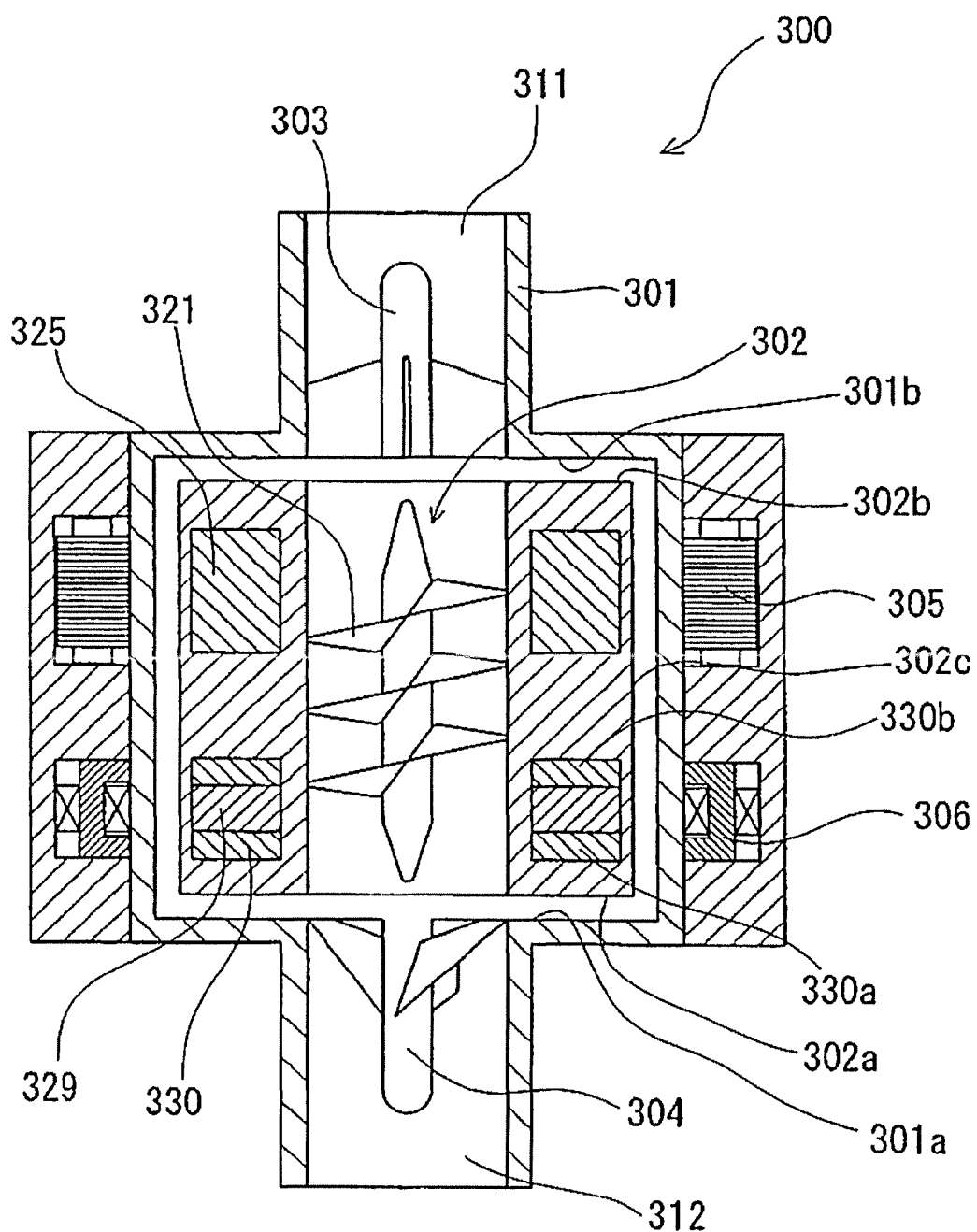
FIG. 20 is a longitudinal cross-sectional view of an example of a blood pump used in the sensorless magnetic bearing type blood pump apparatus according to another embodiment of the present invention.
Figure 21:
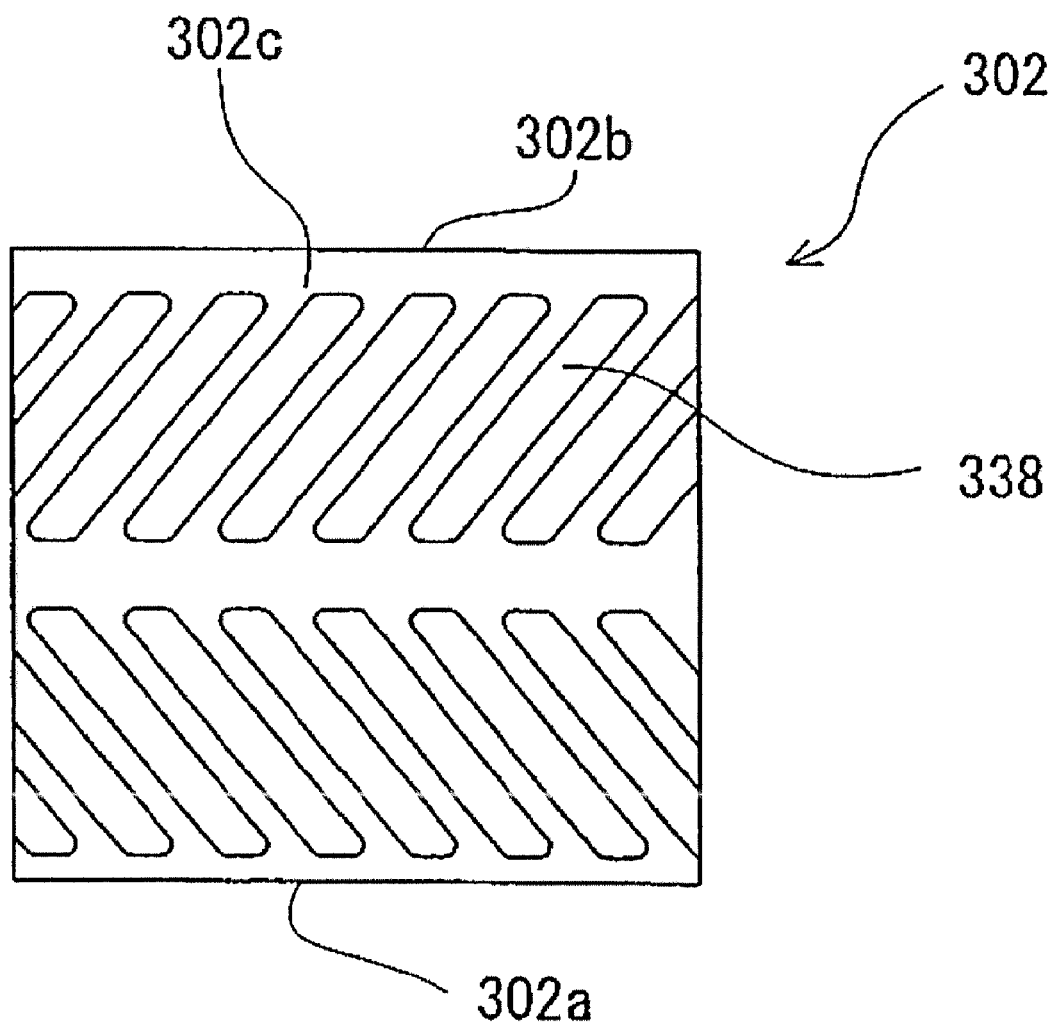
FIG. 21 is a front view of a rotating body used in the blood pump shown in FIG. 20.

FIGS. 20-22 illustrate a blood pump 300 in the form of a radial gap type axial flow pump. The blood pump 300 in this embodiment also includes: a housing 301 having a blood inflow port 311 and a blood outflow port 312; a rotating body 302 provided with magnetic bodies 325 and rotated in the housing 301 in a non-contact condition relative to the inside surface of the housing 301 to feed blood; a rotating body rotational torque generating unit 305 for rotating the rotating body 302 by acting thereon from the outside of the housing 301; a magnetic bearing unit 306 for permitting the rotating body 302 to be rotated in a non-contact condition in the housing 301; and a hydrodynamic bearing section for permitting the rotating body 302 to be rotated in a non-contact condition in the housing 301 when the operation of the magnetic bearing unit 306 is stopped.

In the blood pump 300, the housing 301 is a tubular body enlarged in diameter at a rotating body containing section, as shown in FIG. 20, and is provided with a blood inflow port 311 on the upper end side and with a blood outflow port 312 on the lower end side.

The rotating body 302 is contained in the housing 301 and is hollow cylindrical in shape. The rotating body 302 has a blood conveying fin 321 provided in a hollow section thereof. The rotating body 302 is provided in an inside and peripheral edge part thereof with magnetic bodies 325 to be supplied with a rotating force from the rotating body rotational torque generating unit 305, is provided with second magnetic bodies 329 in an inside and peripheral edge part thereof, and is also provided with third magnetic bodies 330 in proximity to the second magnetic bodies 329. The second magnetic bodies 329 are composed of permanent magnets.

In addition, the housing 301 has a straightener 303 disposed in the vicinity of the rotating body 302 and in the blood inflow port 311, and a diffuser 304 disposed in the vicinity of the rotating body 302 and in the blood outflow port 312.

In the blood pump 300 in this embodiment, the rotating body rotational torque generating unit is composed of a stator coil motor 305 including a plurality of stator coils disposed to surround a side surface of the rotating body 302 so as to attract the magnetic bodies 325 of the rotating body 302 and to rotate the rotating body 302 when energized.

Furthermore, in the blood pump 300 in this embodiment, the non-contact bearing mechanism has magnetic bearing means that includes an electromagnet(s) 306 for attracting the third magnetic bodies 330 or the second magnetic bodies 329 (or both the third magnetic bodies 330 and the second magnetic bodies 329) when energized.

The pump apparatus including the blood pump in this embodiment has a control mechanism like the pump apparatus described in relation to the above-mentioned embodiment. The control mechanism includes: a PWM type electromagnet driving unit for driving the electromagnet(s) 306; a carrier component measuring unit for measuring carrier components of the voltage and current in the PWM type electromagnet driving unit; rotating body position data and modulation factor calculating units for respectively calculating rotating body position data and the modulation factor of a pulse width modulated waveform, by use of carrier wave data measured by the carrier component measuring unit; a rotating body position controlling unit or means for controlling the PWM type electromagnet driving unit by utilizing the rotating body position data calculated by the rotating body position data calculating unit; and a bearing mode changing-over means for effecting transition (change-over) to a hydrodynamic bearing mode by stopping the driving of the PWM type electromagnet driving unit when the modulation factor calculated by the modulation factor calculating unit is outside a predetermined range and for restarting the driving of the PWM type electromagnet driving unit, thereby returning to the magnetic bearing mode, upon confirmation of satisfaction of predetermined conditions after the transition (change-over) to the hydrodynamic bearing mode.

As shown in FIG. 21, the rotating body 302 is provided in its side surface with hydrodynamic grooves 338 constituting a hydrodynamic bearing section. Particularly, the hydrodynamic grooves 338 in this embodiment are grooves arranged in a herringbone pattern. The hydrodynamic grooves 338 are plural in number and are inclined at a predetermined angle relative to the center axis of the rotating body and are arrayed in an annular pattern so that they are arranged at regular or equal intervals. In addition, the hydrodynamic grooves 338 consist of two rows of grooves, and the grooves in the two rows are symmetrical with each other with respect to the center line between the two rows. Therefore, the hydrodynamic grooves 338 are arranged in the so-called herringbone pattern. As illustrated, the grooves in each row are preferably parallel to one another.

Further, as shown in FIG. 22, the rotating body 302 is provided with second hydrodynamic grooves 371 in its bottom surface (the surface facing the inside surface of the housing 301 on the diffuser 304 side) 302a. The second hydrodynamic grooves 371 may alternatively be formed in the inside surface of the housing 301 facing the bottom surface of the rotating body 302. As the second hydrodynamic grooves 371, grooves that are the same as hydrodynamic grooves 38 described in relation to the blood pump 10 above can be used.

The hydrodynamic bearing section is not limited to the hydrodynamic grooves 371, and may include a deformed surface (specially shaped surface) provided in the bottom surface 302a of the rotating body 302 or in the inside surface 301a of the housing 301 facing the bottom surface 302a of the rotating body 302.

Furthermore, in the blood pump 300 in this embodiment, the rotating body 302 is provided with third hydrodynamic grooves in its top surface (the surface facing the inside surface of the housing 301 on the straightener 303 side) 302b. These third hydrodynamic grooves can be similar to those shown in FIG. 22. The third hydrodynamic grooves may alternatively be formed in the inside surface of the housing 301 facing the top surface 302b of the rotating body 302. As the hydrodynamic grooves 338, grooves that are the same as the hydrodynamic grooves 38 or 71 described in relation to the blood pump 10 above can be used.

In addition, the third hydrodynamic bearing section may include a deformed surface (specially shaped surface) provided in the top surface 302b of the rotating body 302 or in the inside surface 301b of the housing 301 facing the top surface 302b of the rotating body 302.

In the blood pump 300 in this embodiment, as shown in FIG. 20, a permanent magnet 329 and two magnetic bodies (iron rings) 330a, 330b for magnetic levitation are embedded in a side surface part of the rotating body 302. In addition, a motor for rotating the rotating body 302 and electromagnets 306 for magnetic levitation are provided in a side part of the housing 301. Specifically, four electromagnets 306 are arranged at regular angular intervals of 90°, like in the blood pump 100 shown in FIG. 13, whereby control in the X direction and the Y direction can be performed. As a result, the required radial gap can be obtained.

In this blood pump 300, no current flows in the electromagnets 306 at the time of rotation in a hydrodynamic bearing mode. However, since the permanent magnet 329 embedded in the rotating body 302 and the cores in the electromagnets 306 attract each other, the impeller moves little in the axial direction, and tends to adhere to some portion of the inside surface of the housing 301 in the radial direction. In this blood pump 300, however, if the rotation can be maintained, when the rotating body 302 comes into proximity to the inside surface of the housing 301a force for spacing the rotating body 302 away from the housing 301 is exerted by the pressure generated by the hydrodynamic grooves 338 provided in the side surface of the rotating body 302 in the proximity area, so that the rotation in a non-contact condition is maintained. Furthermore, the second hydrodynamic grooves 371 and the third hydrodynamic grooves provided respectively in the bottom surface and the top surface of the rotating body 302 ensure that when the rotating body 302 is tending to approach the bottom surface or the top surface of the housing 301, a force in the reverse direction is generated by the pressure generated by the hydrodynamic grooves in each of the bottom and top surfaces of the rotating body 302, whereby the rotation in the non-contact condition is maintained.

The principles, preferred embodiments and other disclosed aspects of the sensorless blood pump apparatus have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A sensorless magnetic bearing type blood pump apparatus comprising:
    a blood pump; and
    a control mechanism for controlling the blood pump;
    the blood pump comprising:
        a housing having a liquid inflow port and a liquid outflow port;
        a rotatable body rotatably positioned in the housing to feed liquid and provided with a first magnetic body;
        a rotating body rotational torque generating unit which attracts the first magnetic body of the rotatable body to rotate the rotatable body;
        a rotating body magnetic bearing unit which magnetically attracts the rotatable body in a direction different from a direction of attraction of the rotatable body by the rotating body rotational torque generating unit to rotate the rotatable body in a non-contact condition in the housing;
        a hydrodynamic bearing section provided in an inside surface of the housing on a side of the rotating body rotational torque generating unit, or in a surface of the rotatable body on a side of the rotating body rotational torque generating unit, to permit the rotatable body to be rotated in a non-contact condition in the housing in a hydrodynamic bearing mode when operation of the rotating body magnetic bearing unit in a magnetic bearing mode is stopped;
        the blood pump apparatus being devoid of any sensor for measuring a position of the rotatable body; and
        the rotating body magnetic bearing unit comprising an electromagnet in the rotatable body for attracting the first magnetic body or a second magnetic body provided separately from the first magnetic body;
    the control mechanism comprising:
        a pulse width modulation type electromagnet driving unit for driving the electromagnet;
        a carrier component measuring unit for measuring carrier components of voltage and current in the pulse width modulation type electromagnet driving unit;
        rotating body position data and modulation factor calculating units which respectively calculate rotating body position data and a modulation factor of a pulse width modulated waveform using carrier wave data measured by the carrier component measuring unit;
        rotating body position controlling means for controlling the pulse width modulation type electromagnet driving unit utilizing the rotating body position data calculated by the rotating body position data calculating unit;
        monitoring means for monitoring a current of the rotating body rotational torque generating unit;
        bearing mode changing-over means for effecting change-over from the magnetic bearing mode to the hydrodynamic bearing mode by stopping driving of the pulse width modulation type electromagnet driving unit when the modulation factor calculated by the modulation factor calculating unit is outside a predetermined range and for restarting the driving of the pulse width modulation type electromagnet driving unit to return to the magnetic bearing mode upon confirmation of satisfaction of predetermined conditions after the change-over to the hydrodynamic bearing mode, the bearing mode changing-over means effecting the return to the magnetic bearing mode by judging that the predetermined conditions are satisfied when the monitoring means determines that the rotating body rotational torque generating unit current is within a current range of the rotating body rotational torque generating unit.

2. The sensorless magnetic bearing type blood pump apparatus as set forth in claim 1, wherein the hydrodynamic bearing section is comprised of hydrodynamic grooves or a deformed surface provided in an inside surface of the housing on the rotating body rotational torque generating unit side, or in a surface of the rotatable body on the rotating body rotational torque generating unit side.

3. The sensorless magnetic bearing type blood pump apparatus as set forth in claim 1, wherein the hydrodynamic bearing section is comprised of hydrodynamic grooves or a deformed surface provided in a surface of the rotatable body on the rotating body magnetic bearing unit side, or an inside surface of the housing facing the rotatable body.

4. The sensorless magnetic bearing type blood pump apparatus as set forth in claim 2, wherein the blood pump comprises second hydrodynamic grooves provided in an inside surface of the housing on the rotating body magnetic bearing unit side, or in a surface of the rotatable body on the rotating body magnetic bearing unit side.

5. The sensorless magnetic bearing type blood pump apparatus as set forth in claim 1, wherein the carrier component measuring unit comprises a voltage resonant circuit, a voltage wave detection circuit, a current resonant circuit, and a current wave detection circuit.

6. The sensorless magnetic bearing type blood pump apparatus as set forth in claim 1, wherein the control mechanism stores a predetermined modulation factor range, and the bearing mode changing-over means effects the change-over to the hydrodynamic bearing mode by stopping the driving of the pulse width modulation type electromagnet driving unit when a modulation factor outside the predetermined modulation factor range is calculated by the modulation factor calculating means.

7. The sensorless magnetic bearing type blood pump apparatus as set forth in claim 1, wherein the bearing mode changing-over means effects the return to the magnetic bearing mode by judging that the predetermined conditions are satisfied upon lapse of a predetermined time after the change-over to the hydrodynamic bearing mode.

8. The sensorless magnetic bearing type blood pump apparatus as set forth in claim 1, wherein the rotating body rotational torque generating unit comprises a rotor having a magnet which attracts the first magnetic body of the rotatable body, and a motor for rotating the rotor.

9. The sensorless magnetic bearing type blood pump apparatus as set forth in claim 1, wherein the rotating body rotational torque generating unit comprises a plurality of stator coils arranged on a circumference of a circle to attract the first magnetic body of the rotatable body and rotate the rotatable body.

10. The sensorless magnetic bearing type blood pump apparatus as set forth in claim 1, wherein the blood pump is either a centrifugal blood pump or an axial flow blood pump.

11. A method for controlling operation of a sensorless magnetic bearing type blood pump apparatus, wherein the sensorless magnetic bearing type blood pump apparatus comprises a blood pump comprised of a housing having a liquid inflow port and a liquid outflow port, and a rotatable body rotatably positioned in the housing to feed liquid and provided with an electromagnet, the method comprising:

rotating the rotatable body in a non-contact condition in the housing in a magnetic bearing mode through operation of a pulse width modulation type electromagnet driving unit which drives the electromagnet;

measuring carrier components of voltage and current in the pulse width modulation type electromagnet driving unit to obtain carrier wave data;

calculating a modulation factor of a pulse width modulated waveform using the carrier wave data;

changing-over from the magnetic bearing mode to a hydrodynamic bearing mode by stopping driving of the pulse width modulation type electromagnet driving unit when the modulation factor is outside a predetermined range and rotating the rotatable body in a non-contact condition in the housing through use of a hydrodynamic bearing section of the blood pump;

monitoring a rotating body rotational torque generating unit current;

restarting the driving of the pulse width modulation type electromagnet driving unit to return to the magnetic bearing mode upon satisfying predetermined conditions after the change-over to the hydrodynamic bearing mode, the predetermined conditions including when the rotating body rotational torque generating unit current is within a current range of the rotating body rotational torque generating unit.

12. The method according to claim 11, further comprising calculating a position data of the rotatable body, and controlling the pulse width modulation type electromagnet driving unit utilizing the calculated position data.

13. The method according to claim 11, wherein the predetermined conditions at which the return to the magnetic bearing mode occurs is lapse of a predetermined time after the change-over to the hydrodynamic bearing mode.

* * * * *